(12) United States Patent  (10) Patent No.: US 7,754,726 B2
Lang et al.  (45) Date of Patent: Jul. 13, 2010

(54) BENZAMIDE DERIVATIVES AS P-38 KINASE INHIBITORS

(75) Inventors: Hengyuan Lang, San Diego, CA (US); Jiong Lan, San Diego, CA (US); Yunfeng Fang, San Diego, CA (US)

(73) Assignee: Novartis AG, Basel (CH)

( * ) Notice: Subject to any disclaimer, the term of this patent is extended or adjusted under 35 U.S.C. 154(b) by 746 days.

(21) Appl. No.: 10/565,452

(22) PCT Filed: Jul. 23, 2004

(86) PCT No.: PCT/US2004/023726

§ 371 (c)(1), (2), (4) Date: May 5, 2006

(87) PCT Pub. No.: WO2005/012241

PCT Pub. Date: Feb. 10, 2005

(65) Prior Publication Data

US 2007/0111999 A1    May 17, 2007

Related U.S. Application Data

(60) Provisional application No. 60/490,096, filed on Jul. 25, 2003.

(51) Int. Cl.
C07D 239/42    (2006.01)
(52) U.S. Cl. .................. 514/256; 544/329
(58) Field of Classification Search ............ 514/256; 544/329
See application file for complete search history.

(56) References Cited

FOREIGN PATENT DOCUMENTS

| WO | WO 01/94312 | * | 12/2001 |
|---|---|---|---|
| WO | 03/032970 | | 4/2003 |
| WO | 03/032971 | | 4/2003 |
| WO | 03/032972 | | 4/2003 |
| WO | 03/032980 | | 4/2003 |
| WO | 03/032986 | | 4/2003 |
| WO | 03/032987 | | 4/2003 |
| WO | 03/033457 | | 4/2003 |
| WO | 03/033482 | | 4/2003 |
| WO | 03/033483 | | 4/2003 |
| WO | 03/068747 | | 8/2003 |
| WO | 03/093248 | | 11/2003 |
| WO | WO 03/093248 | * | 11/2003 |
| WO | 2004/089874 | | 10/2004 |
| WO | 2004/089874 A1 | | 10/2004 |
| WO | 2004/089876 | | 10/2004 |
| WO | 2004/089876 A1 | | 10/2004 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Patani, et al. Chem. Rev., 96, 1996, pp. 3147-3176.*
Definition of derivative. Webster-Merriam Online Dictionary. http://www.merriam-webster.com/dictionary/derivative. Accessed Nov. 18, 2008.*

* cited by examiner

*Primary Examiner*—James O Wilson
*Assistant Examiner*—Douglas M Willis
(74) *Attorney, Agent, or Firm*—Sophie Binet Cross

(57) ABSTRACT

Benzamide combounds of Formula I:

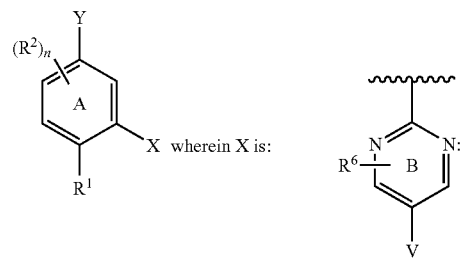

and their compositions for modulating the activity of p38 kinases are provided, including p38α, and p38β kinase. Methods for treating, preventing or ameliorating one or more symptoms of a p38 kinase mediated disease or disorder such as inflammatory diseases, autoimmune diseases, destructive bone disorders, proliferative disorders, angiogenic disorders, infectious diseases, neurodegenerative diseases, and viral diseases are also provided.

13 Claims, No Drawings

BENZAMIDE DERIVATIVES AS P-38 KINASE INHIBITORS

CROSS REFERENCE TO RELATED APPLICATION

This application claims benefit of U.S. Provisional Application No. 60/490,096, filed Jul. 25, 2003, which in its entirety is herein incorporated by reference.

Priority is claimed herein under 35 U.S.C. §119(e) to U.S. Provisional Patent Application No. 60/490,096, filed Jul. 25, 2003, and entitled "p38 KINASE INHIBITORS." The disclosures of the above-referenced application is incorporated by reference herein in its entirety.

FIELD

Provided herein are compounds which have cytokine inhibitory activity. The compounds in certain embodiments are aryl and heteroaryl compounds for treating conditions associated with p38α and β kinases and for treating p38 kinase-associated conditions.

BACKGROUND OF THE INVENTION

A large number of cytokines participate in the inflammatory response, including IL-1, IL6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, 24:1345-1354 (1999); Salituro et al., *Curr. Med. Chem.*, 6:807-823 (1999)]. Evidence in human patients indicates that protein antagonists of cytokines are effective in treating chronic inflammatory diseases, such as, for example, monoclonal antibody to TNF-α (Remicade) [Rankin et al., *Br. J. Rheumatol.*, 34:334-342 (1995)], and soluble TNF-α receptor-Fc fusion protein (Etanercept) [Moreland et al., 25 *Ann. Intern. Med.*, 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinases. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38α, p38β, p38γ, and p38δ. The α and β forms are expressed in inflammatory cells and are key modulators of TNF-α production. Inhibiting the p38α and β enzymes in cells results in reduced levels of TNF-α expression. Also, administering inhibitors of p38α and β in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G. D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

Pyrrolotriazine compounds useful as tyrosine kinase inhibitors are disclosed in U.S. patent application Ser. No. 09/573,829 filed May 18, 2000, assigned to Bristol-Myers Squibb. In addition, pyrrolotriazine kinase inhibitors are disclosed in WO 02/40486, assigned to Bristol-Myers Squibb. Other applications disclosing p38 kinase inhibitors include: WO 03/032970, WO 03/033482, WO03/032971, WO 03/032986, WO 03/032980, WO 03/032987, WO 03/033483, WO 03/033457 and WO 03/032972 are incorporated into this application. Each of the patent applications, patents, and publications referred to herein is incorporated herein by reference.

BRIEF SUMMARY OF THE INVENTION

Provided herein are compounds, compositions and methods of treating, preventing, or ameliorating one or more symptoms of conditions associated with p38 kinase activity. In one embodiment, the compounds for use in the compositions and methods are heteroaryl amides. In another embodiment, the heteroaryl amides are useful as kinase inhibitors, including p38α and p38β kinases.

In one embodiment, the compounds provided herein have formula I:

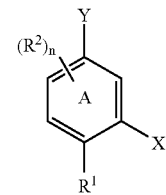

or a pharmaceutically acceptable derivative thereof, wherein X, Y, n, $R^1$ and $R^2$ are elected such that the resulting compound shows p38 kinase activity.

Also provided are pharmaceutical compositions containing a compound of formula I as defined above in combination with a pharmaceutically acceptable carrier.

Methods of treating, preventing or ameliorating one or more symptoms of cytokine mediated disease in a mammal, by administering to a mammalian patient, in need of such treatment, a compound of formula I are provided. Diseases and disorders treated, prevented, or whose symptoms are ameliorated, include, but are not limited to, chronic inflammatory diseases, inflammatory bowel disease, rheumatoid arthritis, psoriasis, multiple sclerosis, endotoxin shock, osteoporosis, Alzheimer's disease, and congestive heart failure.

Methods of preventing or inhibiting inflammatory responses using the compounds and compositions provided herein are also provided.

Further provided are methods of inhibiting p38 kinases, including p38α and p38β kinases, using the compounds and compositions provided herein. Further provided are methods of mediating cytokine response using the compounds and compositions provided herein.

Articles of manufacture are provided containing packaging material, a compound or composition provided herein which is useful for treating, preventing, or ameliorating one or more symptoms of p38 kinase-mediated diseases or disorders, and a label that indicates that the compound or composition is useful for treating, preventing, or ameliorating one or more symptoms of p38 kinase-mediated diseases or disorders.

DETAILED DESCRIPTION

A. Definitions

Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, p38α refers to the enzyme disclosed in Han et al. (1995) *Biochim. Biophys. Acta* 1265(2-3):224-7. As used herein, p38δ refers to the enzyme disclosed in Jiang et al. (1996) *J. Biol. Chem.* 271(30):17920-6. As used herein, p38γ refers to the enzyme disclosed in Li et al. (1996) *Biochem. Biophys. Res. Commun.* 228: 334-340. As used herein, p38δ refers to the enzyme disclosed in Wang et al. (1997) *J. Biol. Chem.* 272(38):23668-74.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, oxalates, benzoates, salicylates, maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, allyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl.

Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

The term "alkyl" refers to straight or branched chain unsubstituted hydrocarbon groups of 1 to 20 carbon atoms, in another embodiment 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. The term "$C_{1-4}$ alkyl" includes a bond and alkyl groups of 1 to 4 carbon atoms.

The term "substituted alkyl" refers to an alkyl group substituted by one to four substituents, in another embodiment, one, two or three substituents, selected from halo, hydroxy, alkoxy, oxo (=O), alkanoyl, aryloxy, alkanoyloxy, amino, alkylamino, arylamino, aralkylamino, disubstituted amines in which the 2 amino substituents are selected from allyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocycles, such as indolyl, imidazolyl, furyl, thienyl, thiazolyl, pyrrolidyl, pyridyl, pyrimidyl and the like. Where the substituent on the allyl is further substituted, it will be with alkyl, alkoxy, aryl, or aralkyl.

When the term alkyl is used in connection with another group, as in heterocycloalkyl or cycloalkylalkyl this means the identified group is bonded directly through an alkyl group which may be branched or straight chain. In the case of substituents, as in "substituted cycloalkylalkyl," the alkyl portion of the group may, besides being branched or straight chain, be substituted as recited above for substituted alkyl groups and/or the connected group may be substituted as recited herein for that group.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups. When the aryl is substituted, each ring of the aryl may be substituted.

The term "substituted aryl" refers to an aryl group substituted by one to four substituents, in another embodiment, one, two or three substituents, selected from alkyl, substituted alkyl, halo, trifluoromethoxy, trifluoromethyl, hydroxy, alkoxy, alkanoyl, alkanoyloxy, amino, arylamino, aralkylamino, dialkylamino, alkanoylamino, thiol, alkylthio, ureido, nitro, cyan, carboxy, carboxyalkyl, carbamyl, alkoxycarbonyl, alkylthiono, arylthiono, arylsulfonylamine, sulfonic acid, alkysulfonyl, sulfonamido, and aryloxy. The substituent may be further substituted by hydroxy, alkyl, alkoxy, aryl, substituted aryl, substituted alkyl or aralkyl.

The term "aralkyl" refers to an aryl group bonded directly through an allyl group, such as benzyl, wherein the alkyl group may be branched or straight chain. In the case of a "substituted aralkyl," the alkyl portion of the group may, besides being branched or straight chain, be substituted as recited above for substituted alkyl groups and/or the aryl portion may be substituted as recited for substituted aryl. Thus, the term "optionally substituted benzyl"

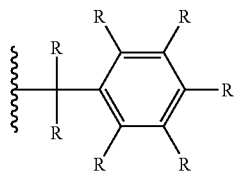

refers to the group wherein each R group may be hydrogen or may also be selected from alkyl, halogen, cyano, nitro, amino, hydroxy, allcoxy, alkylthio, phenyl, benzyl, phenyloxy, and benzyloxy, and other groups recited above. In one embodiment, at least two of these "R" groups are hydrogen. In another embodiment, at least five of the "R" groups are hydrogen.

The term "heteroaryl" refers to an aromatic group for example, which is a 4 to 7 membered monocyclic, 7 to 11 membered bicyclic, or 10 to 15 membered tricyclic ring system, which has at least one heteroatom and at least one carbon atom containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

A "substituted heteroaryl" has one to four substituents on any one or more of the rings comprising the heteraryl group. The substituents may be selected from those 30 recited below for heterocycle groups.

Exemplary monocyclic heteroaryl groups include pyrrolyl, pyrazolyl, pyrazolinyl, imidazolyl, oxazolyl, isoxazolyl, thiazolyl

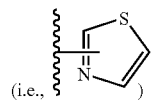

thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzopuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "alkenyl" refers to straight or branched chain hydrocarbon groups of 2 to 20 carbon atoms, in one embodiment 2 to 15 carbon atoms, in another embodiment 2 to 8 carbon atoms, having one to four double bonds, in another embodiment one or two double bonds.

The term "substituted alkenyl" refers to an alkenyl group substituted by one to two substituents selected from halo, hydroxy, alkoxy, alkanoyl, alkanoyloxy, amino, alkylamino, diallcylamino, alkanoylamino, thiol, alkylthio, alkylthiono, alkylsulfonyl, sulfonamido, nitro, cyano, carboxy, carbamyl, substituted carbamyl, guanidino, and substituted and unsubstituted heterocycles, including indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, in one embodiment 2 to 15 carbon atoms, in another embodiment 2 to 8 carbon atoms, having one to four triple bonds in another embodiment one or two triple bonds.

The term "substituted alkynyl" refers to an alkynyl group substituted by a substituent selected from halo, hydroxy, alkoxy, alkanoyl, alkanoyloxy, amino, alkylamino, dialkylamino, alkanoylamino, thiol, alkylsulfonyl, sulfonamido, nitro, cyano, carboxy, carbamyl, substituted carbamyl, adamantyl and substituted or unsubstituted heterocyclo, e.g. imidazolyl, furyl, thienyl, thiazolyl, pyrrolidyl, pyridyl, pyrimidyl and the like.

The term "cycloalkyl" refers to a saturated or partially unsaturated nonaromatic cyclic hydrocarbon ring system, in one embodiment containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, and adamantyl. A "substituted cycloalkyl" is substituted with one or more alkyl or substituted allyl groups as described above, or one or more groups described above as alkyl substituents. The expression "lower cycloalkyl" refers to an unsubstituted saturated or unsaturated nonaromatic cyclic hydrocarbon ring system containing 3 to 5 carbon atoms.

The terms "heterocycle", "heterocyclic" and "heterocyclo" each refer to a fully saturated or unsaturated, aromatic or nonaromatic cyclic group, for example, which is a 4 to 7 membered mono cyclic, 7 to 11 membered bicyclic, or 10 to 15 membered tricyclic ring system, which has at least one heteroatom in at least one carbon atom—containing ring. Thus, the term "heterocycle" includes heteroaryl groups as described above. Each ring of the heterocyclic group containing a heteroatom may have 1, 2 or 3 heteroatoms independently selected from nitrogen, oxygen or sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocycles, such as epoxides and aziridines.

A "substituted heterocycle" will be substituted with one or more alkyl or aralkyl groups as described above, and/or one or more groups described above as alkyl substituents.

Unless otherwise indicated, when reference is made to a specifically-named heterocyclo or heteroaryl, the reference is intended to include those systems having the maximum number of non-cumulative double bonds or less than that maximum number of double bonds. Thus, for example, the term "isoquinoline" refers to isoquinoline and tetrahydroisoquinoline. The term "diazepine" refers to a heterocyclo ring having at least one seven atom ring with two nitrogen atoms in the seven membered ring, including a fully saturated or unsaturated diazepine.

The term "heteroatoms" shall include oxygen, sulfur and nitrogen.

The term "haloalkyl" means an alkyl having one or more halo substituents

The term "fluoromethyl" means a methyl group substituted by one, two, or three fluoro atoms, i.e., $CH_2F$, $CHF_2$ and $CF_3$. The term "fluoroalkyl" means an allyl group having from one to five fluoro atoms, such as pentafluoroethyl.

The term "haloalkoxy" means an alkoxy group having one or more halo substituents. For example, "haloalkoxy" includes —$OCF_3$.zzz The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, substituted alkynyl, substituted aryl, substituted heterocycle, substituted cycloalkyl, and so forth, are as follows: alkoxy is —$OR^a$, alkanoyl is —$C(=O)R^a$, aryloxy is —OAr, alkanoyloxy is —$OC(=O)R^a$, amino is —$NH_2$, alkylamino is NHR$^a$, arylamino is —NHAr, aralkylamino is NH—R$^b$—Ar, disubstituted amine or dialkylamino is NR$^c$R$^d$, alkanoylamino is —NH—C(=O)R$^a$, aroylamino is —NH—C(=O)Ar, aralkanoylamino is NH—C(=O)R$^b$—Ar, thiol is —SH, alkylthio is —SR$^a$, arylthio is —SAr, aralkylthio is —S—R$^b$—Ar, alkylthiono is —S(=O)R$^a$, arylthiono is —S(=O)Ar, aralkylthiono is —S(=O)R$^b$—Ar, alkylsulfonyl is —SO$_{(q)}$R$^a$, arylsulfonyl is —SO$_{(q)}$Ar arylsulfonylamine is —NHSO$_{(q)}$Ar, alkylsulfonylamine is NHSO$_2$R$^a$, aralkylsulfonyl is —SO$_{(q)}$R$^b$Ar, sulfonamido is —SO$_2$NH$_2$, nitro is —NO$_2$, carboxy is —CO$_2$H, carbamyl is —CONH$_2$, substituted carbamyl is —C(O)NHR$^c$ or —C(=O)NR$^c$R$^d$, alkoxycarbonyl is —C(=O)OR$^a$, carboxyalkyl is —R$^b$—CO$_2$H, sulfonic acid is —SO$_3$H, arylsulfonylamine is —NHSO$_{(q)}$Ar, guanidino is

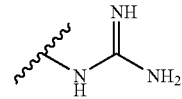

and ureido is

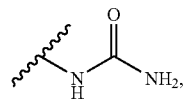

wherein R$^a$ is alkyl as defined above, R$^b$ is alkylene as defined above, R$^c$ and R$^d$ are selected from alkyl, aryl, and aralkyl, Ar is an aryl as defined above, and q is 2 or 3.

Throughout the specification, groups and substituents thereof may be chosen by one skilled in the field to provide stable moieties and compounds.

The compounds of Formula (I, II, II & IV) may form salts. In one embodiment, the salts are pharmaceutically acceptable (i.e. non-toxic, physiologically acceptable) salts, although other salts are also useful, e.g., in isolating or purifying the compounds provided herein. Salt forms of the compounds may be advantageous for improving the compound dissolution rate and oral bioavailability.

All stereoisomers of the compounds provided herein are contemplated, either in admixture or in pure or substantially pure form. The definition of compounds contemplated herein embraces all the possible stereoisomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of Formula (I) may also have prodrug forms. Any compound that will be converted in vivo to provide the bioactive agent (i.e., the compound for formula I) is a prodrug contemplated herein.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also contemplated herein Methods of solvation are generally known in the art.

As used herein, treatment means any manner in which one or more of the symptoms of a disease or disorder are ameliorated or otherwise beneficially altered. Treatment also encompasses any pharmaceutical use of the compounds and compositions herein, such as use for treating p38 kinase mediated diseases or disorders, or diseases or disorders in which p38 kinase activity, including p38α and p38β kinase activity, is implicated.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, $IC_{50}$ refers to an amount, concentration or dosage of a particular test compound that achieves a 50% inhibition of a maximal response, such as modulation of p38α kinase activity, in an assay that measures such response.

B. Compounds

The compounds provided herein for use in the compositions and methods are active in assays that measure p38 kinase activity, including, but not limited to, p38α and p38β kinase activity. In one embodiment, the compounds provided herein have formula I:

or a pharmaceutically acceptable derivative thereof, where:
X is

-continued $R^1$ is selected from hydrogen, halogen, hydroxyl, lower alkyl, lower cycloalkyl, alkynyl, trifluoromethyl, methoxy, trifluoromethoxy, cyano, —$NH_2$, —$NR^4R^5$ and —$OR^4$;

$R^2$ is attached to any available carbon atom of the phenyl ring A and at each occurrence is independently selected from hydrogen, alkyl, lower cycloalkyl, halo, trifluoromethyl, trifluoromethoxy, —OMe, —CN, —$NMe_2$; —S(=O)alkyl, —S(=O)aryl, —$NHSO_2$-aryl-$R^4$, —$NHSO_2$alkyl, —$CO_2R^4$, —$CONH_2$, —$SO_3H$, —S(O)alkyl, —S(O)aryl, —$SO_2NHR^4$, and —NHC(=O)$NHR^4$;

n is 0 or 1;

Y is -L-$R^3$ or $R^{11}$;

$R^3$ is selected from hydrogen, alkyl, —$OR^4$, substituted alkyl, cycloalkyl, —$CR^4$cycloalkyl, heteroaryl, substituted heteroaryl, heterocycle and substituted heterocycle;

L is —C(=O)NH—, —NH(C=O)—, —$SO_2NH$—, —$NHSO_2$—, or —C(=O)—;

$R^{11}$ is an optionally substituted 5-membered heteroaryl;

W is CH or N;

V is -M-$R^{10}$ or $R^{14}$;

M is —C(=O)$NR^4$—, —$NR^4$(C=O)—, —$NR^4$(C=O)$NR^4$—, —$NR^4SO_2$—, or —C(=O)—;

$R^{14}$ is aryl or heteroaryl optionally substituted with up to three $R^{12}$;

P is -Q-$R^{10}$ or $R^{15}$;

Q is —$NR^4$ (C=O)—, —$NR^4$(C=O)$NR^4$—, —$SO_2NR^4$—, —$NR^4SO_2$—, or —C(=O)—;

$R^{15}$ is aryl or heteroaryl optionally substituted with up to three $R^{12}$;

$R^4$ and $R^5$ are each selected independently from hydrogen, lower alkyl and lower cycloalkyl;

$R^6$ is attached to any available carbon atom of the phenyl ring B and at each occurrence is independently selected from hydrogen, alkyl, lower cycloalkyl, halo, trifluoromethyl, trifluoromethoxy, —OMe, —CN, —$NH_2$, —$NMe_2$; —S(=O) alkyl, —S(=O)aryl, —$NHSO_2$-aryl-$R^4$, —$NHSO_2$alkyl, —$CO_2R^4$, —$CONH_2$, —$SO_3H$, —S(O)alkyl, —S(O)aryl, —$SO_2NHR^4$, —NHC(=O)$R^4$, and —NHC(=O)$NHR^4$;

R⁷ and R⁸ are each independently selected from hydrogen, allyl, substituted alkyl, aryl, and cycloalkyl;

R⁹ is hydrogen, alkyl, substituted alkyl or cycloalkyl;

R¹⁰ is alkyl, substituted alkyl, aryl, or —(CH₂)ₜD-(CH₂)ₑ—R¹³;

t is selected from 0, 1, 2 and 3; e is selected from 0, 1, 2 and 3;

D is selected from a bond, an optionally substituted heterocycle, an optionally substituted aryl, —O—, —S—, —(C═O)—, —NR⁴(C═O)—, —(C═O)NR⁴—, —S(O)—, SO₂NR⁴—, SO₂—, and —NR⁴—;

R¹² is selected from R¹⁰, NO₂, CN, lower cycloalkyl, halo, trifluoromethyl, trifluoromethoxy, —OMe, —CN, —NMe₂; —S(═O)alkyl, —S(═O)aryl, —NHSO₂-aryl-R⁴, —NHSO₂-alkyl, —CO₂R⁴, —CONH₂, —SO₃H, —S(O)alkyl, —S(O)aryl, —SO₂NHR⁴, and —NHC(═O)NHR⁴; and R¹³ is selected from an optionally substituted five- to seven-membered heterocyclic ring, an optionally substituted five- to seven-membered heteroaryl ring and an optionally substituted fused bicyclic ring, with the proviso that when Q is CO then Y is not oxadiazolyl and L is not —C(═O)NH— or —NHC(═O).

In certain embodiments, the compounds have formula (II):

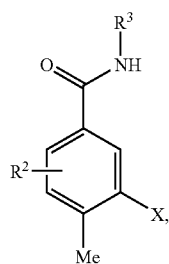

II where R² is selected from hydrogen, methyl and halogen; and R³ is selected from alkyl, —OR⁴, substituted alkyl, cycloalkyl, heteroaryl and substituted heteroaryl, and other variables are as defined elsewhere herein.

In certain embodiments, the compounds have formula (III):

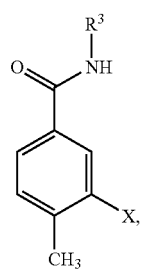

III where the variables are as defined elsewhere herein.

In certain embodiments, the compounds have formula (IV):

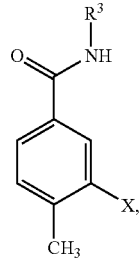

IV wherein R³ is selected from lower alkyl, lower cycloalkyl, heteroaryl, and substituted heteroaryl and other variables are as defined elsewhere herein.

In certain embodiments, the compounds have formula (V):

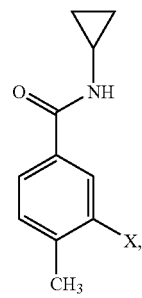

V where the variables are as defined elsewhere herein.

In certain embodiments, the compounds have formula (VI):

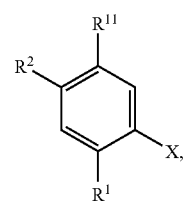

VI where R¹ is selected from methyl, cyclopropyl and halogen; and

R² is selected from hydrogen, methyl and halogen and other variables are as defined elsewhere herein.

In certain embodiments, the compounds have formula (VII):

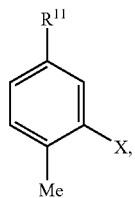

VII where the variables are as defined elsewhere herein.

In certain embodiments, the compounds have formula (VIII):

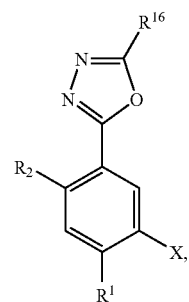

VIII wherein R¹ is selected from methyl, cyclopropyl and halogen; R² is selected from hydrogen, methyl and halogen; R¹⁶ is selected from hydrogen, lower alkyl and lower cycloalkyl and other variables are as defined elsewhere herein.

In certain embodiments, the compounds have formula (IX):

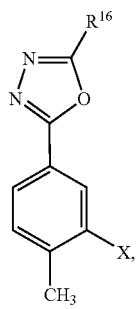

IX where the variables are as defined elsewhere herein.

In certain embodiments, the compounds have formula:

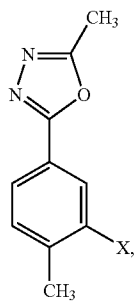

where the variables are as defined elsewhere herein.

In certain embodiments, X is selected from

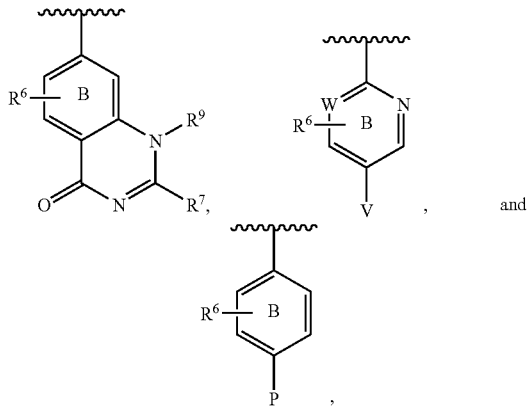

where the variables are as defined elsewhere herein.

In certain embodiments, $R^6$ is lower alkyl or hydrogen. In other embodiments, $R^6$ is methyl or hydrogen. In other embodiments, $R^6$ is methyl. In other embodiments, $R^6$ is hydrogen.

In certain embodiments, W is CH or N. In one embodiment, W is CH. In other embodiment, W is N.

In certain embodiments, V is -M-$R^{10}$ or $R^{14}$.

In certain embodiments, M is —C(=O)N$R^4$—. In other embodiments, M is —C(=O)NH—.

In other embodiments, $R^{10}$ is alkoxyaralkyl. In other embodiments, $R^{10}$ is methoxybenzyl.

In other embodiments, $R^{14}$ is aryl or heteroaryl optionally substituted with up to three $R^{12}$. In other embodiments, $R^{14}$ is heteroaryl optionally substituted with lower alkyl. In other embodiments, $R^{14}$ is oxodiazolyl, optionally substituted with methyl.

In other embodiments, P is —C(=O)—$R^{10}$ or $R^{15}$, where $R^{10}$ is aryl and $R^{15}$ is aryl or heteroaryl optionally substituted with up to three $R^{12}$.

In certain embodiments, $R^1$ is selected from lower allyl, lower cycloalkyl and halogen. In other embodiments, $R^1$ is lower alkyl. In other embodiments, $R^1$ is methyl.

In certain embodiments, $R^2$ is selected from lower alkyl, lower cycloalkyl and halogen. In other embodiments, $R^2$ is hydrogen.

In certain embodiments, L is —C(=O)NH—.

In certain embodiments, $R^3$ is selected from lower alkyl, lower cycloalkyl, heteroaryl, substituted heteroaryl. In other embodiments, $R^3$ is selected from lower alkyl and lower cycloalkyl. In other embodiments, $R^3$ is lower cycloalkyl. In certain embodiments, $R^3$ is cyclopropyl.

C. Preparation of the Compounds

Compounds of formula I can be prepared according to the following schemes and the knowledge of one skilled in the art. Examples of methods useful for the production of compounds provided herein are illustrated in schemes 1-18.

Central to the construction of many of the compounds in this application is the formation of carbon-carbon bonds between aromatic systems using boronic esters or boronic acids and aryl halides by Suzuki reaction.[1] zz Scheme 1 shows a synthetic route to key intermediates and final compounds provided herein.

Scheme 1

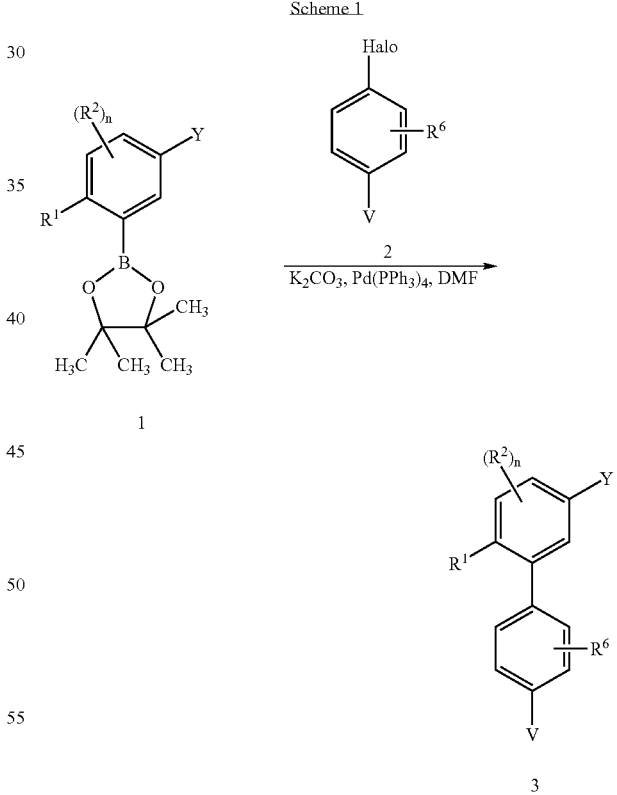

The chemical functionality of the molecule can be changed after the key Suzuki coupling reaction. This is exemplified in Scheme 2. The oxadiazole heterocycle is formed after the carbon-carbon bond formation of the Suzuki reaction. Additional methods are known to those skilled in the art to form heterocycles. For reference, methods disclosed by Dhar et al are cited.[2]zz Scheme 2

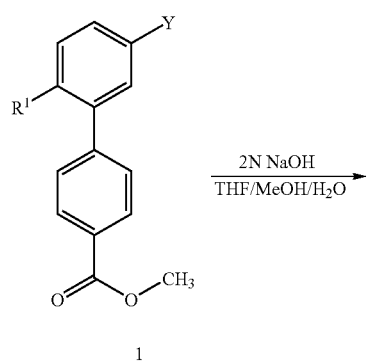

1

$\xrightarrow{\text{2N NaOH}}{\text{THF/MeOH/H}_2\text{O}}$

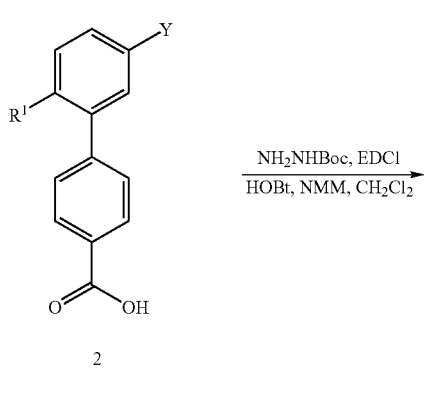

2

$\xrightarrow{\text{NH}_2\text{NHBoc, EDCl}}{\text{HOBt, NMM, CH}_2\text{Cl}_2}$

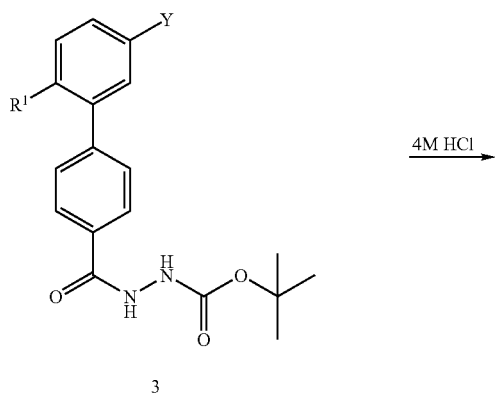

3

$\xrightarrow{\text{4M HCl}}$

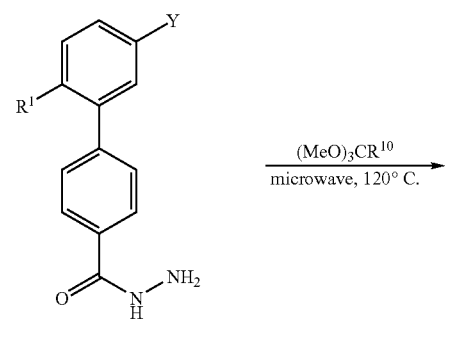

4

$\xrightarrow{\text{(MeO)}_3\text{CR}^{10}}{\text{microwave, 120° C.}}$

-continued

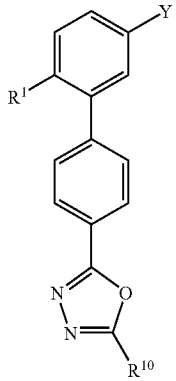

5

Scheme 3 depicts the formation of a triazole heterocycle on a biphenyl moiety.

Scheme 3

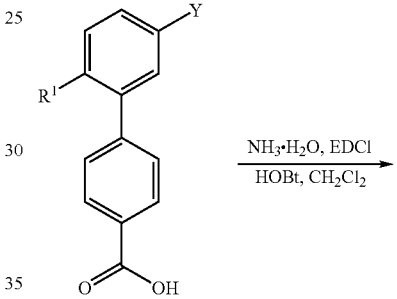

1

$\xrightarrow{\text{NH}_3\cdot\text{H}_2\text{O, EDCl}}{\text{HOBt, CH}_2\text{Cl}_2}$

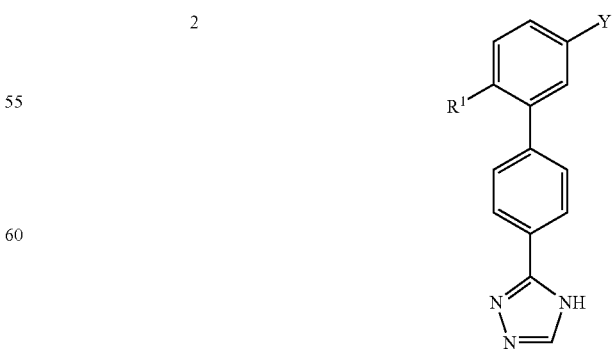

2 i. $\text{Me}_2\text{NCH(OEt)}_2$
ii. $\text{NH}_2\text{NH}_2$, AcOH

3

Scheme 4 depicts the formation of a key carbon bond between an aryl and heteroaryl systems followed by the formation of the terminal 5-membered ring heterocycle.

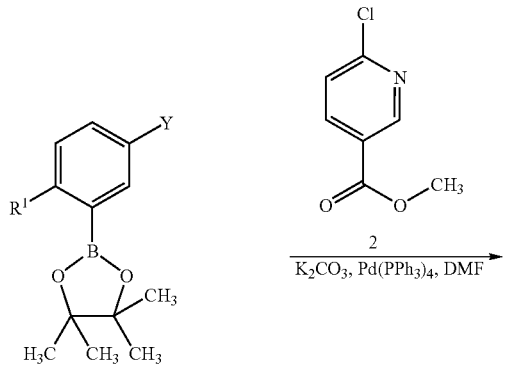

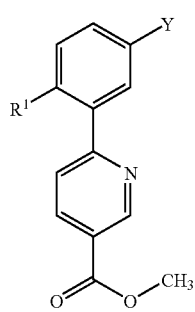

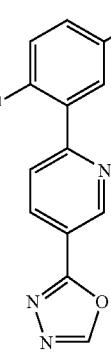

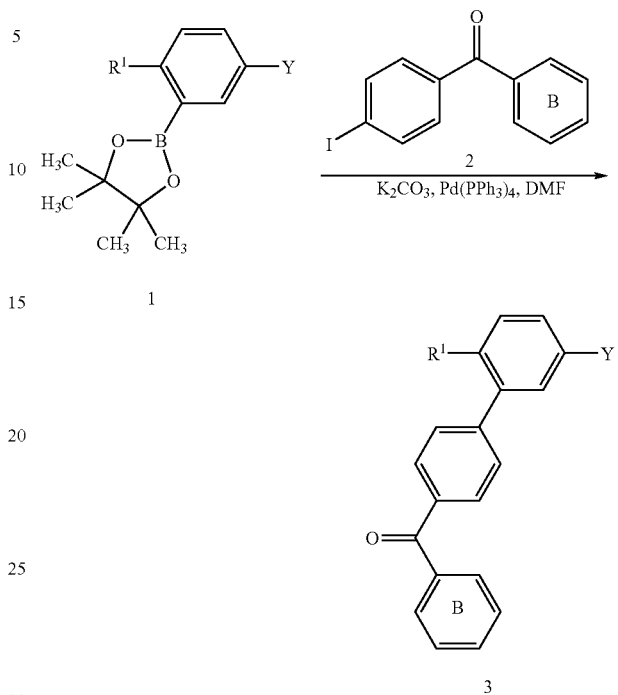

Scheme 5 depicts the formation of the biaryl ketone analogs. The terminal aryl residue (B) may be optionally substituted or may be replaced by an optionally substituted heteroaryl residue.

Scheme 6 depicts the formation of aryl heteroaryl amides. The terminal aryl residue (B) may be optionally substituted or may be replaced by an optionally substituted heteroaryl residue.

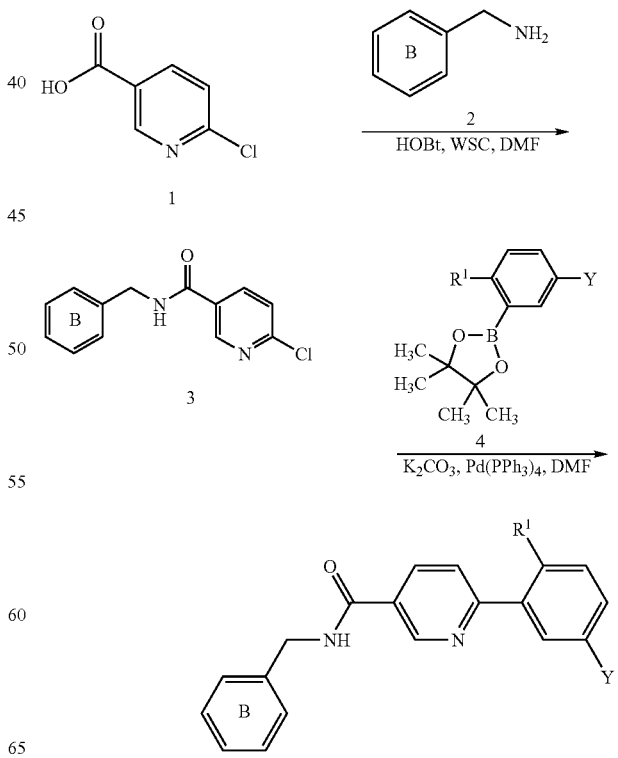

19

Scheme 7

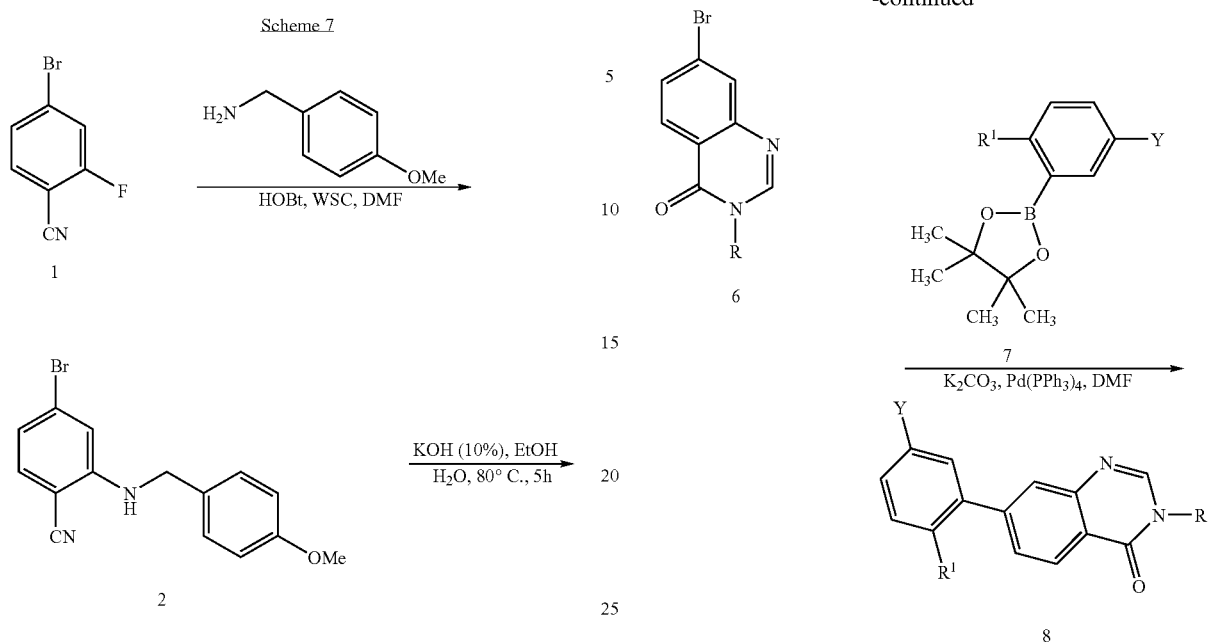

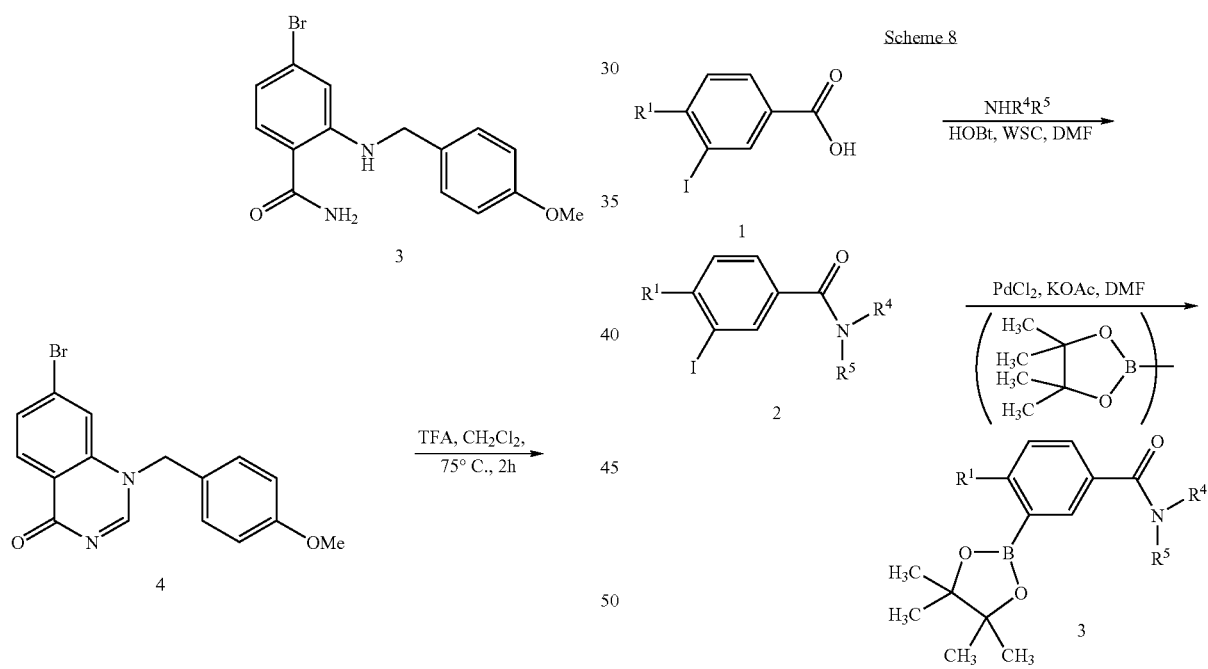

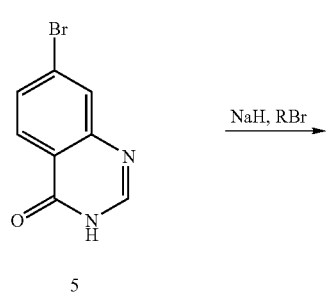

Amines attached to aryl or heteroaryl ring systems are useful as intermediates. There are many methods of preparing such intermediates known to one skilled in the art of organic chemistry. Several methods of preparing amines useful herein are illustrated in schemes 9-11.

Substituted aniline of type (5) can be prepared from commercially available methyl 4-iodobenzoate as depicted in scheme 9. Nitration followed by reduction of the nitro group yields the aniline. Palladium-catalyzed coupling with ethynyltrimethylsilane, followed by desilylation and saponification gives the desired ethynyl-substituted aminobenzoic acid. Coupling with methoxyamine using coupling agent EDC affords the desired aniline (5).

Scheme 9

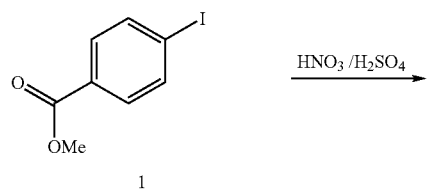
1

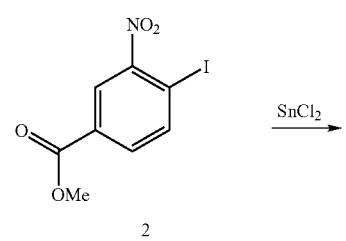
2

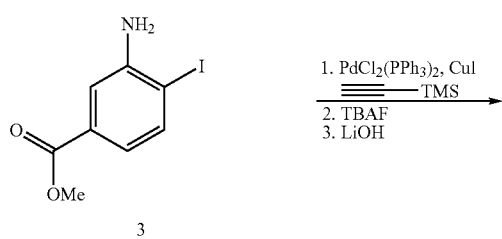
3

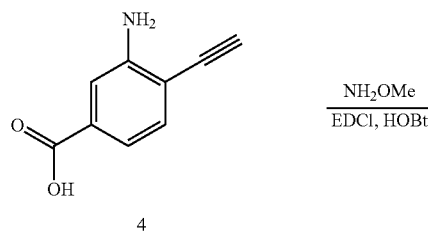
4

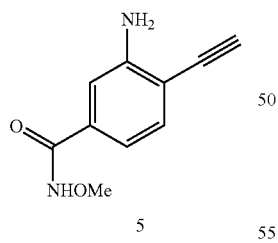
5

Scheme 10

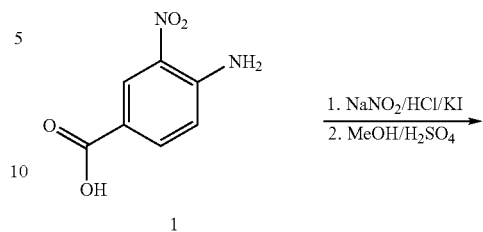
1

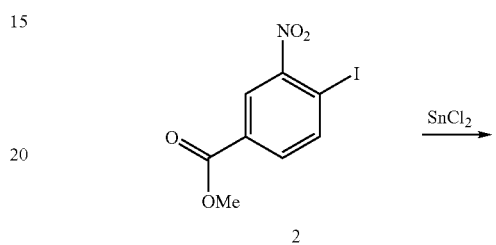
2

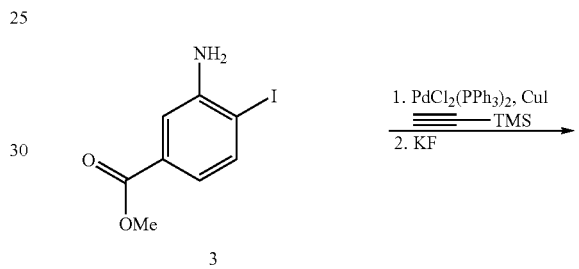
3

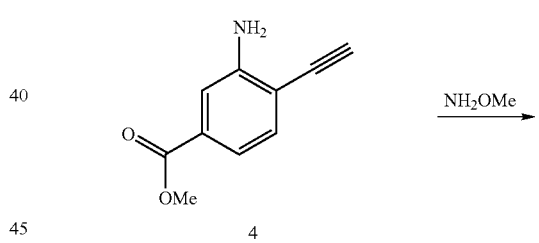
4

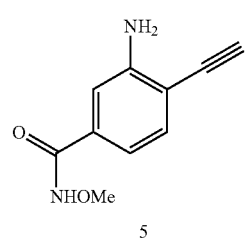
5

Alternatively, substituted aniline of type (5) can be prepared 4-amino-3-nitrobenzoic acid as depicted in scheme 10. Iodide substitution of the aryldiazonium salt, followed by esterification with methanol gives methyl 4-iodo-3-nitrobenzoate. The nitro group can be reduced by SnCl$_4$ to give the desired aniline. Palladium catalyzed coupling with ethynyltrimethylsilane, followed by desilylation and saponification yields the ethynyl-substituted aminobenzoic acid. Coupling with methoxyamine using coupling agent EDC affords the desired aniline (5).

As depicted in scheme 18, substituted aniline of type (4) can be prepared from intermediate methyl 4-iodo-3-nitrobenzoate, which can be synthesized as shown in scheme 10. Palladium catalyzed coupling with vinyltributyltin followed by carbene addition to the resulty styrene double bond gives the cyclopropyl substituted methyl nitrobenzoate. Reduction of the nitro group followed by Boc protection and saponification gives the protected 3-amino-4-cyclopropylbenzoic acid. Coupling with an alkoxyamine using coupling agent EDC affords the desired aniline (4).

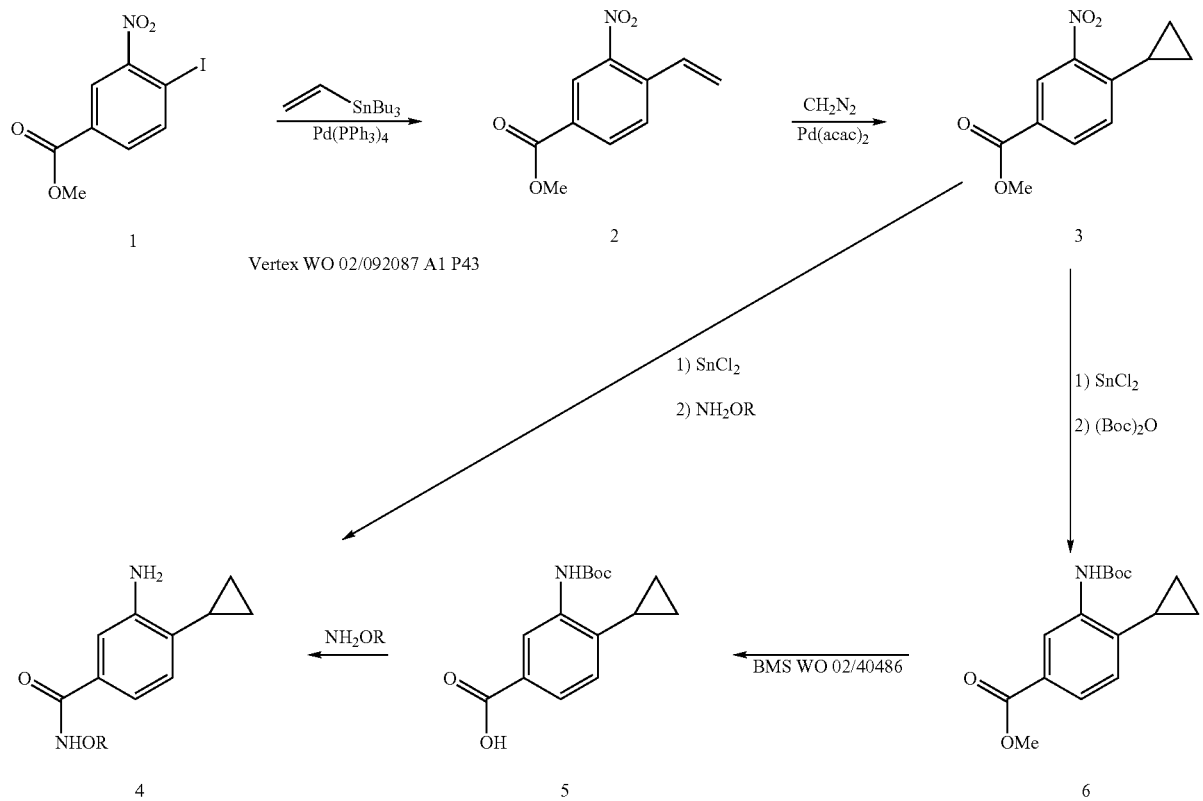

Scheme 11

Vertex WO 02/092087 A1 P43

BMS WO 02/40486

References of additional synthetic methods are as follows:
1) Organic Letters Vol. 4, No. 6, p 979-981 (2002) and references sited therein.
2) Bioorganic and Medicinal Chemistry Letters Vol. 12, 3125-3128 (2002) and references contained therein.

D. Formulation of Pharmaceutical Compositions

Also provided herein is a pharmaceutical composition containing a compound provided herein. The composition can be used, for example, as a medicament. The composition can contain, for example, a pharmaceutically acceptable excipient or carrier. A composition or medicament provided herein can be used for the treatment, prevention or amelioration of one or more symptoms of p38 kinase mediated diseases or disorders, including inflammatory diseases.

Thus, provided herein are pharmaceutical compositions capable of treating p38-kinase-associated conditions, including TNF-α, IL-1, and/or IL-8 mediated conditions, as described above. The compositions may contain other therapeutic agents, as described herein, and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds provided herein may be administered by any means suitable for the condition to be treated, which may depend on the need for site-specific treatment or quantity of drug to be delivered. Topical administration is generally useful for skin-related diseases, and systemic treatment is generally used for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps. Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by, sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound provided herein may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Subjects for treatment include animals, generally mammalian species such as humans, and domestic animals such as dogs, cats, horses, and the like. Thus, when the term "patient" is used herein, this term is intended to include all subjects, in particular mammalian species, including humans, that are affected by mediation of p38 enzyme levels.

Also provided in one embodiment is a process for the manufacture of medicaments which process involves bringing a compound provided herein together with a pharmaceutically acceptable excipient and bringing the mixture into a galenical administration form.

E. Methods of Use of the Compounds and Compositions

In a further embodiment, the compounds provided herein can be used in the treatment, prevention, or amelioration of one or more symptoms of inflammatory diseases. A compound provided herein can be used, in another embodiment, for the manufacture of a medicament for the treatment or prophylaxis of inflammatory diseases.

The compounds provided herein are selective inhibitors of p38 kinase activity, and in particular, isoforms p38α and p38β. Accordingly, compounds provided herein are useful for treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. Provided herein are methods of treating a disease by administering a compound provided herein that inhibits p38 kinase activity. Also provided herein are methods for inhibiting or delaying the onset of a disease or disorder by administering a compound provided herein. Methods provided herein can be used to achieve a full or partial reduction of the symptoms of a disease or disease state, and/or to alleviate, ameliorate, or lessen, the disease or disorder and/or its symptoms. When reference is made herein to inhibition of "p-38α/βkinase," this means that either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

In view of their activity as inhibitors of p38α/β kinase, compounds provided herein are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus. When the terms "p38-associated condition" or "p38-associated disease or disorder" are used herein, each is intended to encompass all of the conditions identified above as if repeated at length, as well as any other condition that is affected by p38 kinase activity.

Thus, provided herein are methods for treating such conditions, involving administering to a subject in need thereof an effective amount of at least one compound provided herein or a pharmaceutically acceptable derivative thereof. The methods of treating p38 kinase-associated conditions may involve administering compounds provided herein alone or in combination with each other and/or other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750 and in S. Ceccarelli et al. (1998) *European Journal of Medicinal Chemistry* 33:943-955; interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds provided herein, may be used, for example, in those amounts indicated in the Physicians' Desk Reference (PDR) or as otherwise determined by one of ordinary skill in the art. In the methods provided herein, such other therapeutic agent(s) may be administered prior to, simultaneously with, or following the administration of the inventive compounds.

The following Examples illustrate embodiments herein, and are not intended to limit the scope of the claims. Abbreviations employed in the Examples are defined below. Compounds of the Examples are identified by the example and step in which they are prepared (for example, "1A" denotes the title compound of step A of Example 1), or by the example only where the compound is the title compound of the example (for example, "2" denotes the title compound of Example 2).

| Abbreviations | |
|---|---|
| Ph = | phenyl |
| Bz = | benzyl |

| -continued | |
|---|---|
| Abbreviations | |
| t-Bu = | tertiary butyl |
| Me = | methyl |
| Et = | ethyl |
| Pr = | propyl |
| Iso-P or i-Pr = | isopropyl |
| MeOH = | methanol |
| EtOH = | ethanol |
| EtOAc = | ethyl acetate |
| Boc = | tert-butyloxycarbonyl |
| CBZ = | carbobenzyloxy or carbobenzoxy or benzyloxycarbonyl |
| DCM or $CH_2Cl_2$ = | dichloromethane |
| DCE = | 1,2-dichloroethane |
| DMF = | dimethyl formamide |
| DMSO = | dimethyl sulfoxide |
| TFA = | trifluoroacetic acid |
| THF = | tetrahydrofuran |
| HATU = | O-(7-Azabenzotriazol-1-yl-N,N,N',N'-tetramethyluronim hexafluorophosphate |
| KOH = | potassium hydroxide |
| $K_2CO_3$ = | potassium carbonate |
| $POCl_3$ = | phosphorous oxychloride |
| KOtBu = | potassium t-butoxide |
| EDC or EDCl = | 1-(3-Dimethylaminopropyl)-3-ethylcarbodiimide hydrochloride |
| DIPEA = | diisopropylethylanmine |
| HOBt = | 1-hydroxybenzotriazole hydrate |
| m-CPBA = | m-chloroperbenzoic acid |
| NaH = | sodium hydride |
| NaOH = | sodium hydroxide |
| $Na_2S_2O_3$ = | sodium thiosulfate |
| $Na_2SO_4$ = | sodium sulfate |
| Pd = | palladium |
| Pd/C = | palladium on carbon |
| min = | minute(s) |
| L = | liter |
| mL = | milliliter |
| μL = | microliter |
| g = | gram(s) |
| mg = | milligram(s) |
| mol = | moles |
| mmol = | millimole(s) |
| meq = | milliequivalent |
| RT or rt = | room temperature |
| ret. t. or $t_R$ = | HPLC retention time (minutes) |
| sat or sat'd = | saturated |

General Methods:

"HPLC (6 minute gradient)" refers to Keystone C18 Beta Basic column, 0.4 mL/min flow rate, 6 minute linear gradient elution (start solvent % B=0; final solvent % B=100), solvent A: acetonitrile+0.025% TFA; solvent B=$H_2O$+ 0.025% TFA.

"HPLC (4 minute gradient)" refers to Keystone C18 Beta Basic column, 0.5 mL/min flow rate, 4 minute linear gradient elution (start solvent % B=0; final solvent % B=100), solvent A: acetonitrile+0.025% TFA; solvent B=$H_2O$+ 0.025% TFA.

The following Examples illustrate embodiments herein, and are not intended to limit the scope of the claims.

EXAMPLE 1

6-Methyl-4'-[1,3,4]oxadiazol-2-yl-biphenyl-3-carboxylic acid cyclopropylamide

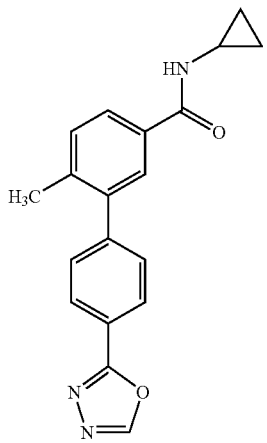

A. N-Cyclopropyl-3-iodo-4-methyl-benzamide

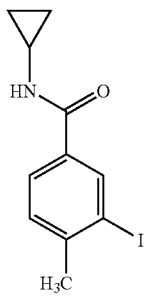

A solution of 3-iodo-4-methylbenzoic acid (10.5 g, 40 mmol), 1-(3-dimethlaminopropyl)-3-ethylcarbodiimide hydrochloride (9.2 g, 48 mmol) and cyclopropylamine (2.6 g, 45.6 mmol) in N,N-dimethylformamide (70 ml) was stirred at room temperature for 4 h. Water (250 mL) was added. The solution was extracted with ethyl acetate (200 mL×2), washed with saturated $K_2CO_3$ solution (200 mL) and water (200 mL). Organic layer was dried over $Na_2SO_4$ and evaporated under reduced pressure to give the desired product (11.8 g, 98%).

HPLC (6 minute gradient) $t_R$=3.39 min; MS m/z 302 (M+H)

B. N-Cyclopropyl-4-methyl-3-(4,4,5,5-tetramethyl-[1,3,2]dioxaborolan-2-yl)-benzamide

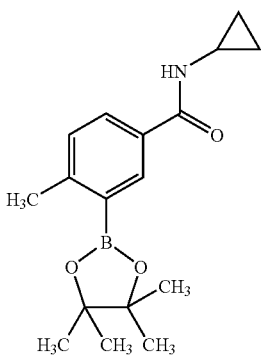

To a solution of the compound from part A (4.52 g, 15 mmol) and bis(pinacolato)diboron (4.05 g, 16 mmol) in 50 mL of dry N,N-dimethylformamide was added potassium acetate (4.4 g, 45 mmol) and followed by $PdCl_2$(pddf) (612 mg, 0.75 mmol). After the reaction mixture was stirred at 95° C. for 5 hours, the reaction mixture was allowed to cool to room temperature. And then 100 mL of water was added. The resulting mixture was extracted with ethyl acetate (2×150 mL). The combined organic layers were washed with water (20 mL), brine (20 mL), dried over $MgSO_4$, and the solvents were evaporated. The residue was purified by chromatography (hexanes:ethyl acetate=2:1) to give the desired product as a colorless solid (3.1 g, 69%).

$^1$H NMR (300 MHz, $CDCl_3$): δ 7.97 (d, J=1.9 Hz, 1H), 7.81 (dd, J=2.1, 7.9 Hz, 1H), 7.23 (d, J=8.0 Hz, 1H), 6.29 (brs., 1H), 2.90 (m, 1H), 2.56 (s, 3H), 1.36 (s, 12H), 0.85 (m, 2H), 0.64 (m, 2H) ppm.

HPLC (4 minute gradient) $t_R$=2.62 min; MS m/z 302 (M+H).

C. 5'-Cyclopropylcarbamoyl-2'-methyl-biphenyl-4-carboxylic acid methyl ester

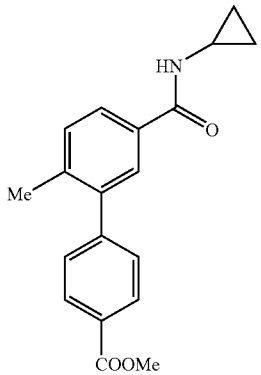

To a solution of 4-iodo-benzoic acid methyl ester (262 mg, 1.0 mmol) and the compound from part B (301 mg, 1.0 mmol) in 3 mL of dry N,N-dimethylformamide was added potassium carbonate (276 mg, 2.0 mmol) and followed by $Pd(PPh_3)_4$ (58 mg, 0.05 mmol). After the reaction mixture was stirred at 100° C. for 2 hours, the reaction mixture was allowed to cool to room temperature. The solvent was removed under reduced pressure. The residue was diluted with 80 mL of ethyl acetate and washed with water (10 mL) and brine (10 mL), dried over $MgSO_4$, and the solvents were evaporated. The residue was purified by chromatography (hexanes:ethyl acetate=2:1) to give a colorless solid (280 mg, 91%)

$^1$H NMR (300 MHz, $CDCl_3$): δ 8.07 (d, J=8.1 Hz, 2H), 7.68 (dd, J=1.9, 7.9 Hz, 1H), 7.60 (d, J=1.8 Hz, 1H), 7.37 (d, J=8.1 Hz, 2H), 7.31 (d, J=8.0 Hz, 1H), 6.53 (brs., 1H), 3.94 (s, 3H), 2.89 (m, 1H), 2.27 (s, 3H), 0.85 (m, 2H), 0.62 (m, 2H) ppm.

HPLC (4 minute gradient) $t_R$=2.39 min; MS m/z 310 (M+H).

D. 5'-Cyclopropylcarbamoyl-2'-methyl-biphenyl-4-carboxylic acid

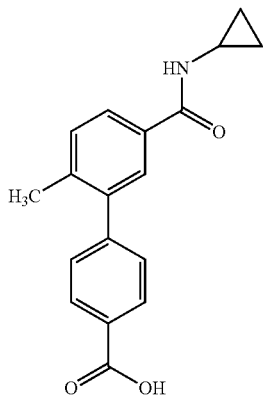

To a solution of the compound from part C (270 mg, 0.87 mmol) in 3 mL of tetrahydrofuran, 1 mL of methanol and 1 mL of water was added sodium hydroxide (2M, 1.3 mL, 2.62 mmol) at 20° C. The reaction mixture was stirred at that temperature overnight and then the clear solution was neutralized by dropwise addition of 2N aqueous hydrochloric acid. The resulting mixture was extracted with ethyl acetate (2×40 mL). The combined organic layers were washed with water (10 mL) and brine (10 mL), dried over MgSO$_4$, and the solvents were evaporated to give the desired compounds as a colorless solid (220 mg, 86%), which was used to the next step without further purification.

$^1$H NMR (300 MHz, CDCl$_3$): δ 8.17 (d, J=8.5 Hz, 2H), 7.69 (dd, J=2.0, 8.0 Hz, 1H), 7.61 (d, J=1.9 Hz, 1H), 7.44 (d, J=8.5 Hz, 2H), 7.36 (d, J=7.9 Hz, 1H), 6.26 (brs., 1H), 2.91 (m, 1H), 2.31 (s, 3H), 0.92 (m, 2H), 0.62 (m, 2H) ppm.

HPLC (4 minute gradient) t$_R$=1.91 min; MS m/z 296 (M+H).

E. N'-(5'-Cyclopropylcarbamoyl-2'-methyl-biphenyl-4-carbonyl)-hydrazinecarboxylic acid tert-butyl ester

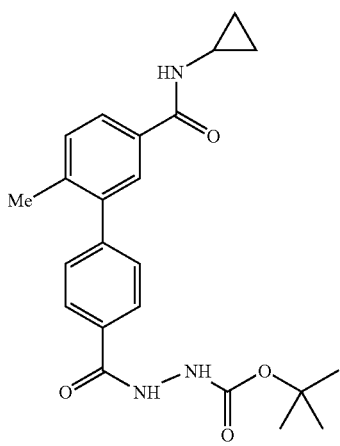

To a solution of the compound from part D (59 mg, 0.20 mmol) and the hydrazine (33 mg, 0.25 mmol) in 2 mL of dry methylene chloride was added 1-hydroxybenzotriazole (46 mg, 0.30 mmol), 1-(3-dimethylaminopropyl)-3-ethylcarbodiimide hydrochloride (57 mg, 0.30 mmol) and 4-methylmorpholine (61 mg, 0.6 mmol) at 20° C. The reaction mixture was stirred at 20° C. for 3 hours. The solvent was removed under reduced pressure. The residue was diluted with 60 mL of ethyl acetate and washed with water (10 mL), 2N aqueous HCl (10 mL), sat. aqueous NaHCO$_3$ (10 mL) and brine (10 mL), dried over MgSO$_4$, and the solvents were evaporated to give the desired compounds as a colorless solid (75 mg, 91%), which was pure enough to be used to the next step without further purification.

$^1$H NMR (300 MHz, CDCl$_3$): δ 8.28 (brs., 1H), 7.86 (d, J=8.3 Hz, 2H), 7.66 (dd, J=1.9, 7.9 Hz, 1H), 7.55 (d, J=1.9 Hz, 1H), 7.35 (d, J=8.3 Hz, 2H), 7.31 (d, J=8.1 Hz, 1H), 6.79 (brs., 1H), 6.38 (brs., 1H), 2.90 (m, 1H), 2.25 (s, 3H), 1.51 (s, 9H), 0.85 (m, 2H), 0.62 (m, 2H) ppm.

HPLC (4 minute gradient) t$_R$=2.10 min; MS m/z 410 (M+H)

F. 4'-Hydrazinocarbonyl-6-methyl-biphenyl-3-carboxylic acid cyclopropylamide

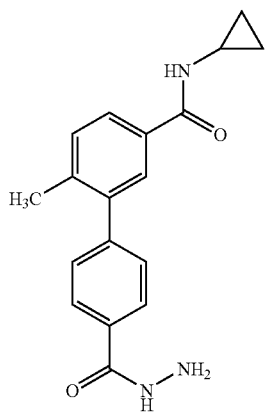

To a solution of the compound from part E (70 mg, 0.17 mmol) in 2 mL of methanol was added HCl (4N, 0.42 mL, 0.17 mmol) in 1,4-dioxane. The reaction mixture was stirred at room temperature for 2 hours and then concentrated under reduced pressure to give a colorless solid (52 mg, 88%).

G. 6-Methyl-4'-[1,3,4]oxadiazol-2-yl-biphenyl-3-carboxylic acid cyclopropylamide

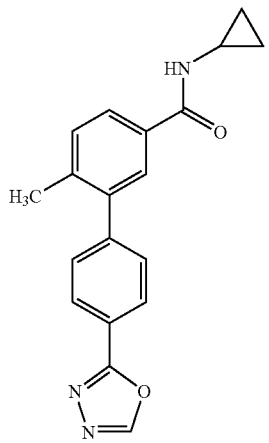

The mixture of the compound from part F (15 mg, 0.044 mmol) in 0.5 mL of trimethyl orthoformate was stirred at 120° C. in microwave for 10 minutes. The solvent was removed under reduced pressure. The residue was diluted with 30 mL of ethyl acetate and washed with sat. aqueous NaHCO$_3$ (10 mL), water (10 mL), and brine (10 mL), dried over MgSO$_4$, and the solvents were evaporated. The residue was purified by preparative TLC sheet (hexanes:ethyl acetate=1:1) to give the desired product as a colorless solid (12 mg, 87%).

$^1$H NMR (300 MHz, CDCl$_3$): δ 8.50 (s, 1H), 8.15 (d, J=8.6 Hz, 2H), 7.67 (dd, J=2.0, 7.9 Hz, 1H), 7.63 (d, J=1.9 Hz, 1H), 7.48 (d, J=8.6 Hz, 2H), 7.35 (d, J=7.9 Hz, 1H), 6.30 (brs., 1H), 2.90 (m, 1H), 2.31 (s, 3H), 0.86 (m, 2H), 0.63 (m, 2H) ppm.

HPLC (4 minute gradient) t$_R$=1.92 min; MS m/z 320 (M+H).

H. 6-Methyl-4'-[1,3,4]oxadiazol-2-yl-biphenyl-3-carboxylic acid cyclopropylamide An Alternative Synthesis of Compound 1

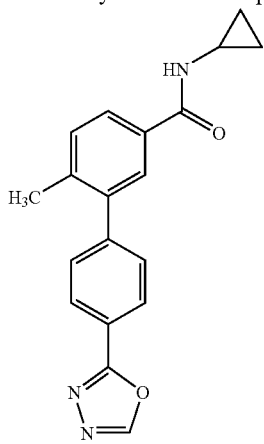

To a solution of the compound from part C (130 mg, 0.42 mmol) in 2 mL of methanol was added 2 mL of hydrazine monohydrate. The reaction mixture was stirred at room temperature for 1 hour. The solvents were removed to give a foam (120 mg). To a solution of this foam (100 mg, 0.32 mmol) in 3 mL of trimethyl orthoformate was added one drop of concentrated HCl. The reaction mixture was stirred at 120° C. in microwave for 10 minutes. The solvent was removed under reduced pressure. The residue was diluted with 80 mL of ethyl acetate and washed with sat. aqueous NaHCO$_3$ (10 mL), water (10 mL), and brine (10 mL), dried over MgSO$_4$, and the solvents were evaporated. The residue was purified by chromatography (hexanes:ethyl acetate=1:1) to give the desired product as a colorless solid (89 mg, 79% for two steps)

EXAMPLE 2

6-Methyl-4'-(5-methyl-[1,3,4]oxadiazol-2-yl)-biphenyl-3-carboxylic acid cyclopropylamide

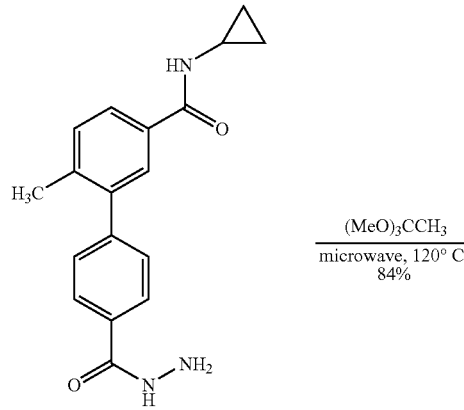

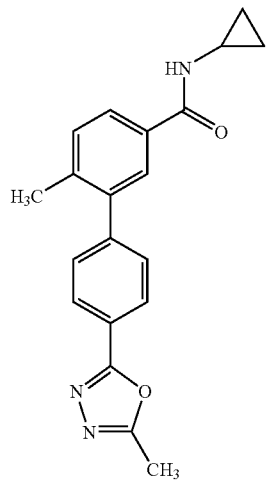

The mixture of the compound from part 1F (21 mg, 0.061 mmol) in 1.5 mL of trimethyl orthoacetate was stirred at 120° C. in microwave for 10 minutes. The solvent was removed under reduced pressure. The residue was diluted with 30 mL of ethyl acetate and washed with sat. aqueous NaHCO$_3$ (10 mL), water (10 mL), and brine (10 mL), dried over MgSO$_4$, and the solvents were evaporated. The residue was purified by preparative TLC sheet (hexanes:ethyl acetate=1:1) to give the desired product as a colorless solid (12 mg, 87%).

HPLC (4 minute gradient) t$_R$=2.10 min; MS m/z 334 (M+H).

EXAMPLE 3

6-Methyl-4'-(4H-[1,2,4]triazol-3-yl)-biphenyl-3-carboxylic acid cyclopropylamide

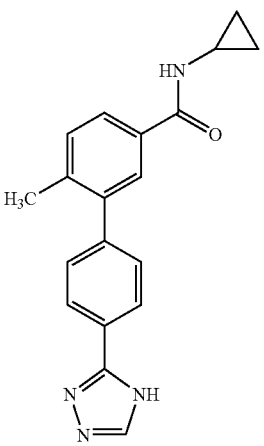

A. 6-Methyl-biphenyl-3,4'-dicarboxylic acid 4'-amide 3-cyclopropylamide

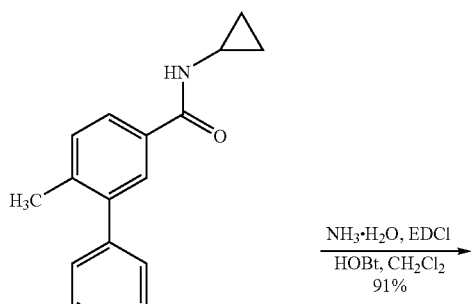

To a solution of the compound from 1D (50 mg, 0.17 mmol) and the ammonium hydroxide (30%, 0.3 mL) in 2 mL of methylene chloride was added 1-hydroxybenzotriazole (39 mg, 0.25 mmol) and 1-(3-dimethylaminopropyl)-3-ethylcarbodiimide hydrochloride (49 mg, 0.25 mmol) at 20° C. The reaction mixture was stirred at 20° C. for 4 hours. The solvent was removed under reduced pressure. The residue was diluted with 60 mL of ethyl acetate and washed with water (10 mL), and brine (10 mL), dried over MgSO$_4$, and the solvents were evaporated. The residue was purified by preparative TLC sheet (hexanes:ethyl acetate=1:1) to give the desired product as a colorless solid (12 mg, 91%)

HPLC (4 minute gradient) $t_R$=1.68 min; MS m/z 295 (M+H).

B. 6-Methyl-4'-(4H-[1,2,4]triazol-3-yl)-biphenyl-3-carboxylic acid cyclopropylamide

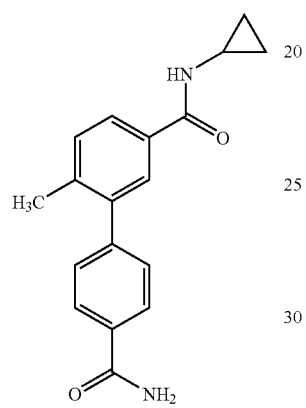

A mixture of the compound from part A (20 mg, 0.068 mmol) in 1.2 mL of N,N-dimethylformamide diethyl acetal was stirred at 80° C. for 3 hours. The solvent was removed under reduced pressure. The residue was dissolved in 1 mL of acetic acid and anhydrous hydrazine (4.4 mg, 0.136 mmol) was added to the mixture. The reaction mixture was stirred at 90° C. for 2 hours. The solvent was removed under reduced pressure. The crude product was purified by preparative TLC sheet (methylene chloride:mathanol=10:1) to give the desired product as a colorless solid (15 mg, 69%).

HPLC (4 minute gradient) $t_R$=1.73 min; MS m/z 319 (M+H).

EXAMPLE 4

N-Cyclopropyl-4-methyl-3-(5-[1,3,4]oxadiazol-2-yl-pyridin-2-yl)-benzamide

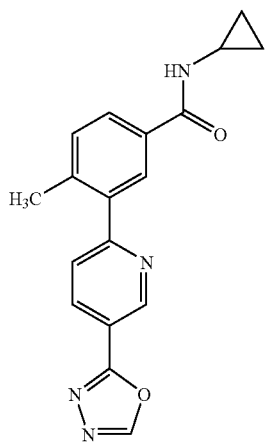

A. 6-(5-Cyclopropylcarbamoyl-2-methyl-phenyl)-nicotinic acid methyl ester

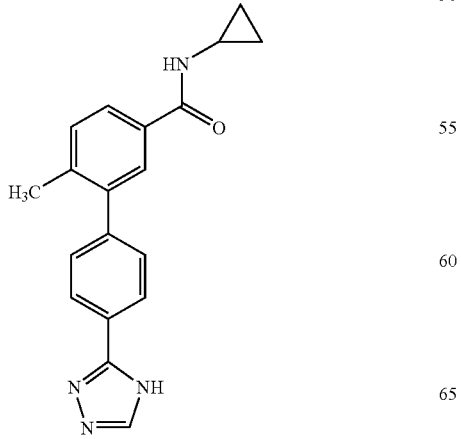

To a solution the 6-chloro-nicotinic acid methyl ester (410 mg, 2.40 mmol) and the compound from 1B (602 mg, 2.0 mmol) in 10 mL of dry N,N-dimethylformamide was added potassium carbonate (663 mg, 4.8 mmol) and followed by Pd(PPh$_3$)$_4$ (115 mg, 0.10 mmol). After the reaction mixture was stirred at 95° C. for 2 hours, the reaction mixture was allowed to cool to room temperature. The solvent was removed under reduced pressure. The residue was diluted with 100 mL of ethyl acetate and washed with water (10 mL) and brine (10 mL), dried over MgSO$_4$, and the solvents were evaporated. The residue was purified by chromatography (hexanes:ethyl acetate=1:1) to give the desired product as a colorless solid (320 mg, 52%).

HPLC (4 minute gradient) $t_R$=1.91 min; MS m/z 311 (M+H).

B. N-Cyclopropyl-3-(5-hydrazinocarbonyl-pyridin-2-yl)-4-methyl-benzamide

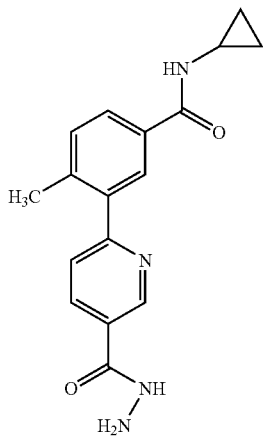

To a solution of the compound from part A (80 mg, 0.26 mmol) in 2 mL of methanol was added 2 mL of hydrazine monohydrate. The reaction mixture was stirred at room temperature for 2 hour. The solvents were removed to give the desired compound as a foam (72 mg).

C. N-Cyclopropyl-4-methyl-3-(5-[1,3,4]oxadiazol-2-yl-pyridin-2-yl)-benzamide

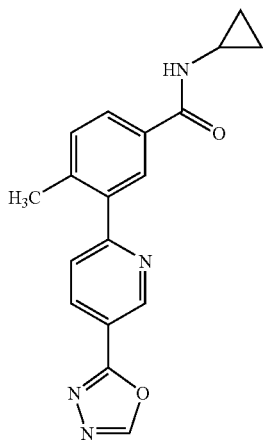

To a solution of the compound from part B, 2 mL of trimethyl orthoformate was added one drop of concentrated HCl. The reaction mixture was stirred at 120° C. in microwave for 10 minutes. The solvent was removed under reduced pressure. The residue was diluted with 30 mL of ethyl acetate and washed with sat. aqueous NaHCO$_3$ (10 mL), water (10 mL), and brine (10 mL), dried over MgSO$_4$, and the solvents were evaporated. The residue was purified by preparative TLC sheet (methylene chloride:methanol=10:1) to give the desired product as a colorless solid (12 mg, 52% for two steps).

HPLC (4 minute gradient) $t_R$=1.65 min; MS m/z 321 (M+H).

EXAMPLE 5

N-Cyclopropyl-4-methyl-3-[5-(5-methyl-[1,3,4]oxadiazol-2-yl)-pyridin-2-yl]-benzamide

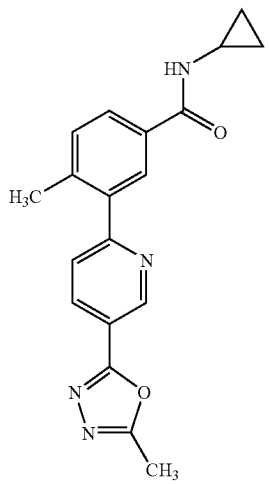

To the compound from 4B (20 mg, 0.065 mmol) in 2 mL of trimethyl orthoacetate was added one drop of concentrated HCl. The reaction mixture was stirred at 120° C. in microwave for 10 minutes. The solvent was removed under reduced pressure. The residue was diluted with 30 mL of ethyl acetate and washed with sat. aqueous NaHCO$_3$ (10 mL), water (10 mL), and brine (10 mL), dried over MgSO$_4$, and the solvents were evaporated. The residue was purified by preparative TLC sheet (methylene chloride:methanol=10:1) to give the titled compound as a colorless solid (14 mg, 65%)

HPLC (4 minute gradient) $t_R$=1.69 min; MS m/z 335 (M+H).

EXAMPLE 6

3-(3-Benzyl-4-oxo-3,4-dihydro-quinazolin-7-yl)-N-cyclopropyl-4-methyl-benzamide

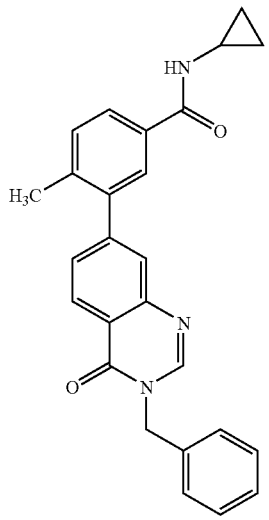

A. 4-Bromo-2-(4-methoxy-benzylamino)-benzonitrile

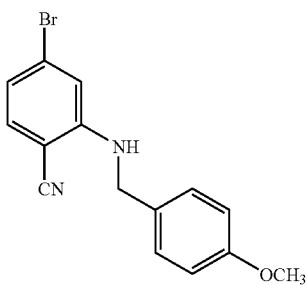

A solution of 5-bromo-2-fluorobenzonitrile (3 g), 4-methoxybenzylamine (2.2 g), and triethyl amine (3 ml) in DMSO (5 ml) was heated at 120° C. for 5 h. The solution was partitioned between water and ethyl acetate. The combined organic extract was washed with brine, dried over $Na_2SO_4$ and concentrated. The residue was chromatographed to give the desired product (2.6 g, 81%) HPLC (6 minute gradient) $t_R$=4.33 min; MS m/z 315.09, 317.08 $(M+H)^+$

B. 4-Bromo-2-(4-methoxy-benzylamino)-benzamide

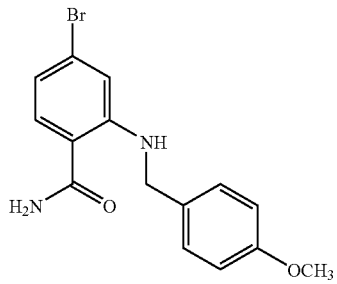

The compound from part A was heated in a KOH solution (10%) of $EtOH/H_2O$, 50%, 100 ml) at 80° C. for 5 h. The resulting precipitate was filtrated and dried to yield 4-bromo-2-(4-methoxy)benzylbenzamide (2.0 g, 95%).

C. 7-Bromo-1-(4-methoxy-benzyl)-1H-quinazolin-4-one

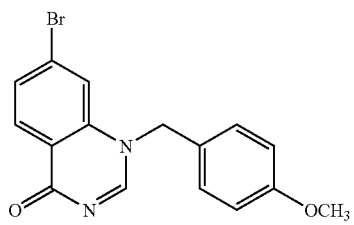

The compound from part B (1.8 g) was heated in a solution of N,N-dimethylformamide dimethyl acetal (3 ml) and DMF (2 ml) at 130° C. for 4 h. Then the solvent was removed and water (2 ml) was added. The precipitate was filtrated and washed with water and 50% ethyl acetate/hexane. 1.55 g of the desired compound is obtained (yield: 75%).

$^1$H NMR (300 MHz, $CDCl_3$) δ 3.84 (s, 3H), 5.24 (s, 2H), 6.97 (d, 2H, J=6.7 Hz), 7.20 (d, 2H, J=6.7 Hz), 7.48 (s, 1H), 7.60 (d, 1H, J=8.5 Hz), 8.22 (d, 1 H, J=8.5 Hz), 8.34 (s, 1H)

D. 7-Bromo-3H-quinazolin-4-one

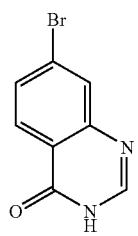

The compound from part C was treated with TFA/dichloroethane (50%, 3 ml) at 75° C. for 2 h. The solvent was removed with nitrogen and ethyl acetate was added. The resulting precipitate was filtered to yield the desired compound (1.0 g, 96%).

HPLC (4 minute gradient) $t_R$=1.61 min; MS m/z 225.25, 227.21 $(M+H)^+$

E. 3-Benzyl-7-bromo-3H-quinazolin-4-one

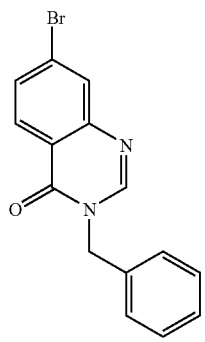

To a solution of the compound from part D (225 mg, 1 mmol) in dry DMF (4 ml) was added sodium hydride (30 mg). The solution was cooled down to 0° C. and benzyl bromide (171 mg) was added. Then the mixture was allowed to react at room temperature for 10 min. after adding water (15 ml), the precipitate was filtrated and washed with water and dried in air. 170 mg of desired product was obtained (yield: 54%). HPLC (4 minute gradient) $t_R$=2.54 min; MS m/z 315.27, 317.0 $(M+H)^+$ F. 3-(3-Benzyl-4-oxo-3,4-dihydro-quinazolin-7-yl)-N-cyclopropyl-4-methyl-benzamide

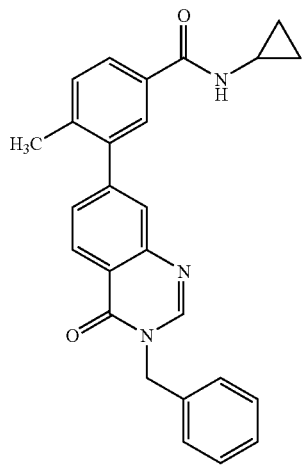

To a solution of the compound from part E (157.5 mg, 0.5 mmol), the compound from 1B (150 mg, 0.5 mmol) and K$_2$CO$_3$ (100 mg) in DMF (5 ml) under nitrogen was added Pd(PPh$_3$)$_4$ (40 mg). The mixture was heated at 95° C. for 3 h. Water (8 ml) was added and the solution was extracted with ethyl acetate (5 ml×2) and dried over Na$_2$SO$_4$. Evaporation of the solvent give a residue which is separated by column chromatography (Hexane:EtOAc=1:1). 146 mg of the desired product was obtained (yield: 71%). HPLC (4 minute gradient) $t_R$=2.15 min; MS m/z 410.47 (M+H)$^+$

EXAMPLE 7

N-Cyclopropyl-3-[3-(2,6-dichloro-benzyl)-4-oxo-3,4-dihydro-quinazolin-7-yl]-4-methyl-benzamide

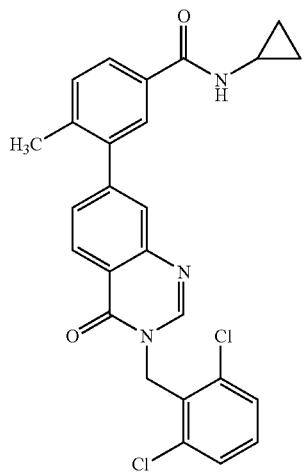

A. 7-Bromo-3-(2,6-dichloro-benzyl)-3H-quinazolin-4-one

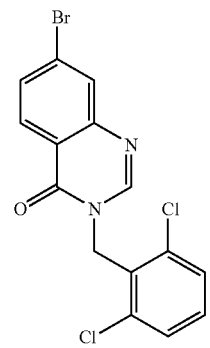

To a solution of the compound from 6D (113 mg, 0.5 mmol) in dry DMF (2 ml) was added sodium hydride (20 mg). The solution was cooled down to 0° C. and 2,6-dichlorobenzy chloride (100 mg, 0.0) was added. Then the mixture was allowed to react at room temperature for 10 min. after adding water (4 ml), the precipitate was filtrated and washed with water and dried in air. 117 mg of desired product was obtained (yield: 61%). HPLC (4 minute gradient) $t_R$=3.11 min; MS m/z 383.40, 385.13, 386.93 (M+H)$^+$ B. N-Cyclopropyl-3-[3-(2,6-dichloro-benzyl)-4-oxo-3,4-dihydro-quinazolin-7-yl]-4-methyl-benzamide

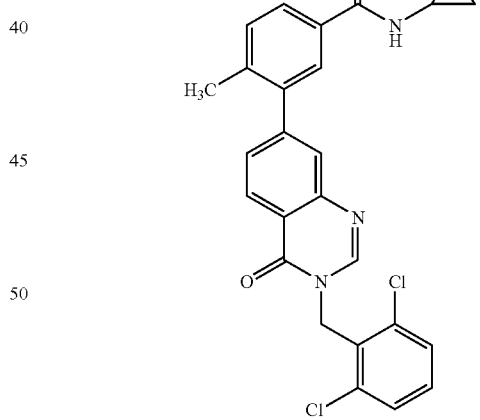

To a solution of the compound from part A (38.5 mg, 0.1 mmol), the compound from 1B (30 mg, 0.1 mmol) and K$_2$CO$_3$ (30 mg) in DMF (2 ml) under nitrogen was added Pd(PPh$_3$)$_4$ (10 mg). The mixture was heated at 95° C. for 3 h. Water (3 ml) was added and the solution was extracted with ethyl acetate (4 ml×2) and dried over Na$_2$SO$_4$. Evaporation of the solvent give a residue which is separated by preparative TLC plate (DCM:EtOAc=1:1). 46 mg of the desired product was obtained (yield: 95%). HPLC (4 minutes gradient) $t_R$=2.59 min; MS m/z 478.80, 480.33

EXAMPLE 8

N-Cyclopropyl-3-[3-(3,4-dichloro-benzyl)-4-oxo-3,4-dihydro-quinazolin-7-yl]-4-methyl-benzamide

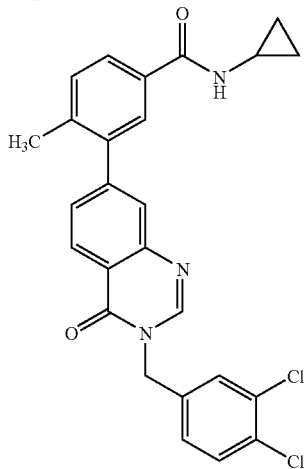

A. 7-Bromo-3-(3,4-dichloro-benzyl)-3H-quinazolin-4-one

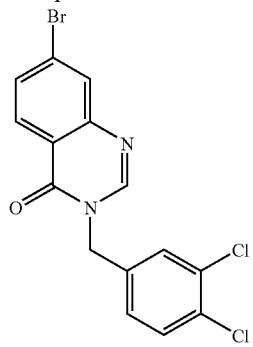

To a solution of the compound f from 6D (113 mg, 0.5 mmol) in dry DMF (2 ml) was added sodium hydride (20 mg). The solution was cooled down to 0° C. and 3,4-dichlorobenzy bromide (120 mg, 0.5 mmol)) was added. Then the mixture was allowed to react at room temperature for 10 min. after adding water (4 ml), the precipitate was filtrated and washed with water and dried in air. 110 mg of desired product was obtained (yield: 57%). HPLC (4 minute gradient) $t_R$=3.24 min; MS m/z 383.33, 385.07, 386.87 (M+H]$^+$ B. N-Cyclopropyl-3-[3-(3,4-dichloro-benzyl)-4-oxo-3,4-dihydro-quinazolin-7-yl]-4-methyl-benzamide

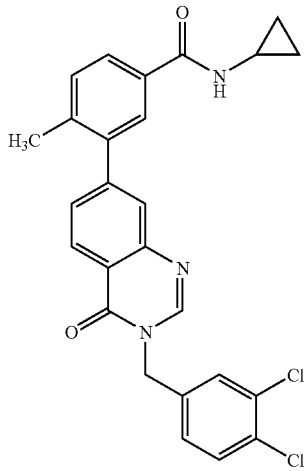

To a solution of the compound from part A (38.5 mg, 0.1 mmol), compound 1B (30 mg, 0.1 mmol) and $K_2CO_3$ (30 mg) in DMF (2 ml) under nitrogen was added Pd(PPh$_3$)$_4$ (10 mg). The mixture was heated at 95° C. for 3 h. Water (3 ml) was added and the solution was extracted with ethyl acetate (4 ml×2) and dried over Na$_2$SO$_4$. Evaporation of the solvent give a residue which is separated by preparative TLC plate (DCM: EtOAc=1:1). 46 mg of the desired product was obtained (yield: 90%). HPLC (4 minute gradient) $t_R$=2.78 min; MS m/z 478.80, 480.33 (M+H]$^+$

EXAMPLE 9

N-Cyclopropyl-3-[3-(4-methoxy-benzyl)-4-oxo-3,4-dihydro-quinazolin-7-yl]-4-methyl-benzamide

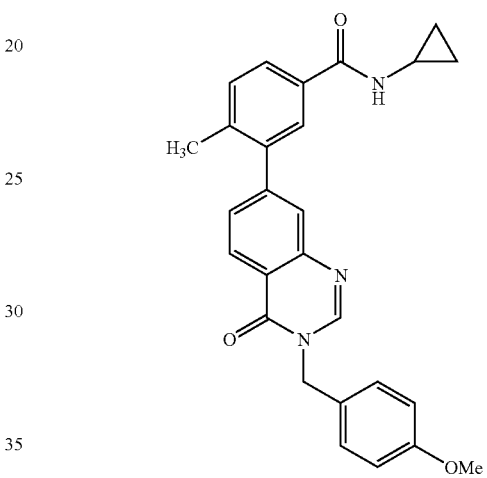

A. 7-Bromo-3-(4-methoxy-benzyl)-3H-quinazolin-4-one

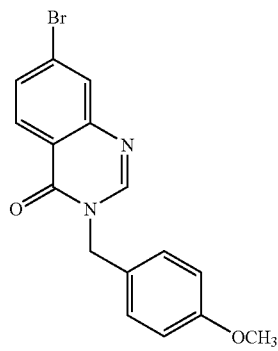

To a solution of the compound 6D (113 mg, 0.5 mmol) in dry DMF (2 ml) was added sodium hydride (20 mg). The solution was cooled down to 0° C. and 4-methoxycarbonyl-benzy bromide (114 mg) was added. Then the mixture was allowed to react at room temperature for 10 min. after adding water (4 ml), the precipitate was filtrated and washed with water and dried in air. 130 mg of desired product was obtained (yield: 67.5%). HPLC (4 minute gradient) $t_R$=2.42 min; MS m/z 373.33, 375.07 (M+H]$^+$ B. N-Cyclopropyl-3-[3-(4-methoxy-benzyl)-4-oxo-3,4-dihydro-quinazolin-7-yl]-4-methyl-benzamide

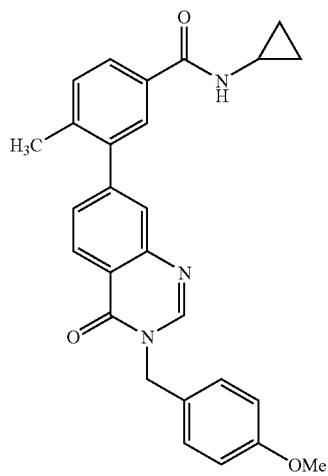

To a solution of the compound from part A (37 mg, 0.1 mmol), compound 1B (30 mg, 0.1 mmol) and $K_2CO_3$ (30 mg) in DMF (2 ml) under nitrogen was added $Pd(PPh_3)_4$ (10 mg). The mixture was heated at 95° C. for 3 h. Water (3 ml) was added and the solution was extracted with ethyl acetate (4 ml×2) and dried over $Na_2SO_4$. Evaporation of the solvent give a residue which was separated by preparative TLC plate (DCM:EtOAc=1:1). 46 mg of desired product was obtained (yield: 68%).

HPLC (4 minute gradient) $t_R$=2.12 min; MS m/z 468.33 $(M+H)^+$

EXAMPLE 10

N-Cyclopropyl-4-methyl-3-(4-oxo-3,4-dihydro-quinazolin-7-yl)-benzamide

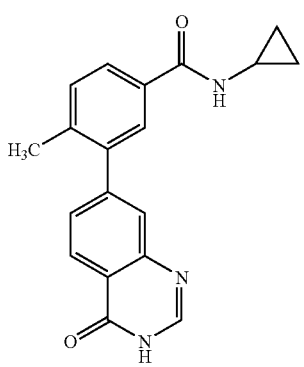

To a solution of the compound 6D (23 mg, 0.1 mmol), compound 1B (30 mg, 0.1 mmol) and $K_2CO_3$ (30 mg) in DMF (2 ml) under nitrogen was added $Pd(PPh_3)_4$ (10 mg). The mixture was heated at 95° C. for 3 h. Water (3 ml) was added and the solution was extracted with ethyl acetate (4 ml×2) and dried over $Na_2SO_4$. Evaporation of the solvent give a residue which was separated by preparative TLC plate (DCM:EtOAc=1:1). 23 mg of title compound was obtained (yield: 72%).

HPLC (4 minute gradient) $t_R$=1.61 min; MS m/z 320.15 $(M+H)^+$

EXAMPLE 11

4'-Benzoyl-6-methyl-biphenyl-3-carboxylic acid cyclopropylamide

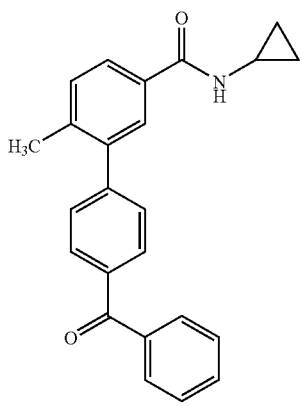

To a solution of 4-iodobenzophenone (62 mg, 0.2 mmol), 1B (60 mg, 0.2 mmol) and $K_2CO_3$ (50 mg) in DMF (2 ml) under nitrogen was added $Pd(PPh_3)_4$ (20 mg). The mixture was heated at 100° C. for 2 h. Water (4 ml) was added and the solution was extracted with ethyl acetate (5 ml×2) and dried over $Na_2SO_4$. Evaporation of the solvent give a residue which is separated by preparative TLC plate (Hexane:EtOAc=1:1). 53 mg of the desired product was obtained (yield: 75%).

HPLC (6 minute gradient) $t_R$=4.15 min; MS m/z 355.95 $(M+H)^+$

EXAMPLE 12

6-(5-Cyclopropylcarbamoyl-2-methyl-phenyl)-N-(4-methoxy-benzyl)-nicotinamide

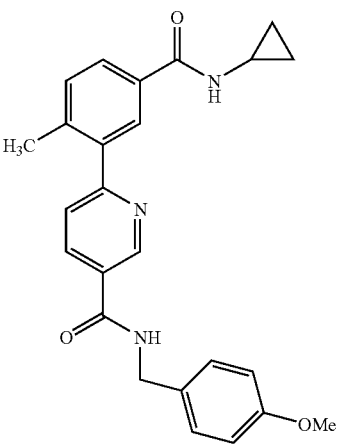

A. 6-Chloro-N-(4-methoxy-benzyl)-nicotinamide

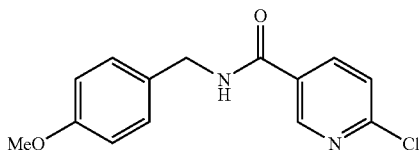

A solution of 6-chloronicotinic acid (473 mg, 3 mmol), 4-methoxybenzylamine (412 mg, 3 mmol), 1-(3-dimethlaminopropyl)-3-ethylcarbodiimide hydrochloride (700 mg, 3.6 mmol) and HOBt (200 mg)) in DMF (15 ml) was stirred at room temperature for 3 h. Water (100 ml) was added. The solution was extracted with ethyl acetate (150 ml×2), washed with saturated $K_2CO_3$ solution (100 ml) and water (200 ml). Organic layer was dried over $Na_2SO_4$ and evaporated under reduced pressure to give the desired product (810 mg, 97%). HPLC (6 minute gradient) $t_R$=3.12 min; MS m/z 275.00, 276.95 $(M+H)^+$

B. 6-(5-Cyclopropylcarbamoyl-2-methyl-phenyl)-N-(4-methoxy-benzyl)-nicotinamide

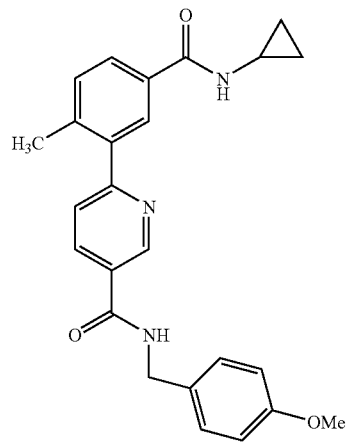

To a solution of the compound from part A (28 mg, 0.1 mmol), compound 1B (30 mg, 0.1 mmol) and $K_2CO_3$ (30 mg) in DMF (2 ml) under nitrogen was added $Pd(PPh_3)_4$ (10 mg). The mixture was heated at 95° C. for 3 h. Water (3 ml) was added and the solution was extracted with ethyl acetate (4 ml×2) and dried over $Na_2SO_4$. Evaporation of the solvent gave a residue which is separated by preparative TLC plate (EtOAc). 32 mg of the desired product was obtained (yield: 76%). HPLC (6 minute gradient) $t_R$=3.01 min; MS m/z 416.16 $(M+H)^+$

EXAMPLE 13

N-(4-Methoxybenzyl)-2-[(5-cyclopropylaminocarbonyl)-2-methylphenyl]-4-aminopyrimidine-5-carboxyamide

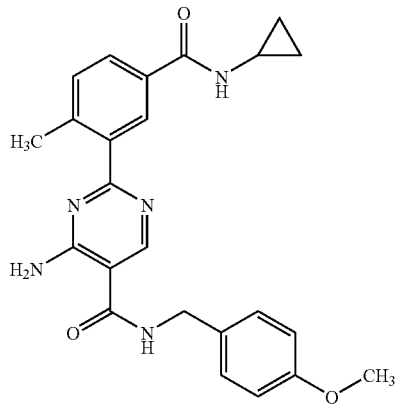

A. Ethyl 4-amino-2-methylmercaptopyrimidine-5-carboxylate

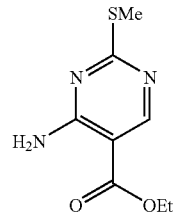

Iodomethane (2.6 g, 18 mmol) was added to the hot solution (~50° C.) of ethyl 4-amino-2-mercaptopyrimidine-5-carboxylate (3.0 g, 15 mmol) in N,N-dimethylformamide (150 mL) and stirred at room temperature for 20 min. Solvent was removed in vacuo and the solid residue was washed by water. After dried in vacuo, desired product was obtained as a white solid (3.1 g, 97%).

HPLC (4 minute gradient) $t_R$=2.14 min; MS m/z 214.1 $(M+H)^+$

B. 4-Amino-2-methylmercaptopyrimidine-5-carboxylic acid

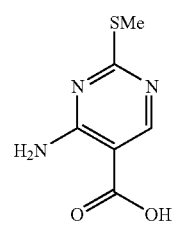

4-Amino-2-methylmercaptopyrimidine-5-carboxylate (1.5 g, 7 mmol) was suspended in the solution of lithium hydroxide (340 mg, 14 mmol) in methanol (10 mL) and water (5 mL) and stirred at 60° C. over night. Solid was filtered out and filtrate was collected. Solvent was removed under reduce pressure. Residue was dissolved in water and was neutralized by acetic acid till pH~5. White solid thus formed was filtered out and dried in vacuo (0.72 g, 55%).

HPLC (4 minute gradient) $t_R$=0.55 min; MS m/z 186.08 (M+H)$^+$

C. N-(4-Methoxybenzyl)4-amino-2-methylmercapto-pyrimidine-5-carboxyamide

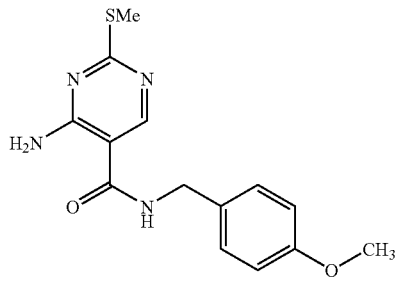

To a solution of 4-amino-2-methylmercaptopyrimidine-5-carboxylic acid (185 mg, 1 mmol) and p-methoxybenzyl amine (164 mg, 1.2 mmol) in N,N-dimethylformamide was added 1-hydroxybenzotriazole (92 mg, 92 mmol) and 1-(3-dimethylaminopropyl)-3-ethylcarboiimide hydrochloride (229 mg, 1.2 mmol). The reaction mixture was stirred at room temperature over night. The solvent was removed under reduce pressure. The residue was dissolved in ethyl acetate (30 mL) and washed by water (30 mL) and brine (30 mL), dried over sodium sulfate, and the solvent was evaporated. The residue was purified by column chromatography (hexanes:ethyl acetate=1:1) to give the desired product as a white powder (245 mg, 81%).

HPLC (4 minute gradient) $t_R$=2.09 min; MS m/z 305.08 (M+H)$^+$

D. 5-Cyclopropylaminocarbonyl-2-methylboronic acid

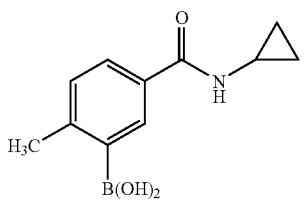

Sodium periodate (4.8 g, 22.5 mmol) was added to the solution of N-cyclopropyl-4-methyl-3-(4,4,5,5-tetramethyl-[1,3,2]dioxaborolan-2-yl)benzamide (2.25 g, 7.5 mmol) in tetrahydrofuran (80 mL) and water (20 mL). The mixture was stirred until homogeneous. Then 2N hydrochloro acid (3.0 mL) was added and stirred at room temperature over night. Tetrahydrofuran was removed in vacuo and the residue was suspended in ethyl acetate (100 mL), washed by water (100 mL), brine (100 mL), dried over sodium sulfate. Solvent was evaporated to give the desired product as a white solid (1.4 g, 85%).

HPLC (4 minute gradient) $t_R$=1.30 min; MS m/z 219.9 (M+H)$^+$

E. N-(4-Methoxybenzyl)-2-[(5-cyclopropylaminocarbonyl)-2-methylphenyl]-4-aminopyrimidine-5-carboxyamide

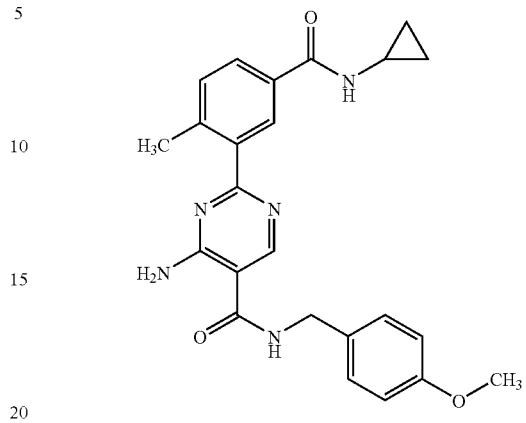

5-Cyclopropylaminocarbonyl-2-methylboronic acid (209 mg, 0.96 mmoL), tris(dibenzylideneacetone)dipalladium (0) (37 mg, 0.004 mmol), tris(2-furyl)phosphine (74 mg, 0.4 mmol) and copper (I) thiophene-2-carboxylate (198 mg, 1.6 mmol) were put in the flask and flushed with nitrogen. N-(4-Methoxybenzyl)4-amino-2-methylmercaptopyrimidine-5-carboxyamide (245 mg, 0.8 mmol) in tetrahydrofuran (10 mL) was added to the flask and stirred at 50° C. in the nitrogen atmosphere over night. Solvent was removed in vacuo. The residue was suspended in ethyl acetate (50 mL) and washed by conc. aminohydroxide (20 mL), brine (50 mL) and dried over sodium sulfate. The residue was purified by column chromatography (hexanes:ethyl acetate=1:1) to give the desired product as a light yellow solid (49 mg, 14%).

HPLC (4 minute gradient) $t_R$=2.04 min; MS m/z 432.36 (M+H)$^+$

EXAMPLE 14

3'-Amino-4'-benzoyl-6-methyl-biphenyl-3-carboxylic acid cyclopropylamide

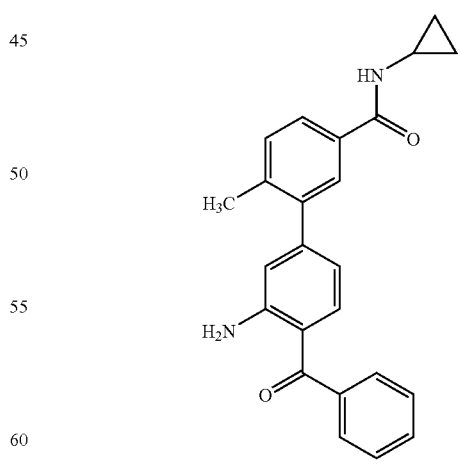

To a solution the (2-Amino-4-bromo-phenyl)-phenyl-methanone (276 mg, 1.0 mmol) and N-Cyclopropyl-3-iodo-4-methyl-benzamide (301 mg, 1.0 mmol) in 5 mL of methyl sulfoxide was added potassium carbonate (276 mg, 2.0 mmol) and followed by Pd(PPh$_3$)$_4$ (58 mg, 0.05 mmol). After the reaction mixture was stirred at 95° C. for 4 hours, the reaction mixture was allowed to cool to room temperature and 10 mL of water was added to the mixture. The resulting mixture was extracted with ethyl acetate (3×50 mL). The combined organic layers washed with water (10 mL) and brine (10 mL), dried over MgSO$_4$, and the solvents were evaporated. The residue was purified by chromatography (hexanes:ethyl acetate=1:1) to give the desired compound as a colorless solid (180 mg, 49%).

HPLC (6 minute gradient) $t_R$=3.89 min; MS m/z 371 (M+H).

EXAMPLE 15

N-Cyclopropyl-4-methyl-3-(2-oxo-4-phenyl-1,2-dihydro-quinazolin-7-yl)-benzamide

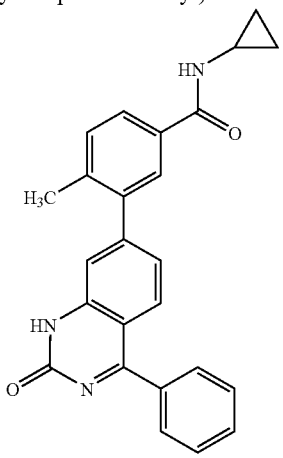

The mixture of 3'-Amino-4'-benzoyl-6-methyl-biphenyl-3-carboxylic acid cyclopropylamide from Example 14 (19 mg, 0.051 mmol) and urea (3.7 mg, 0.062 mmol) in 0.5 mL acetic acid was stirred at 120° C. for 4 hours. The solvents were removed under reduced pressure. The crude product was purified by preparative TLC sheet (methylene chloride:methanol=10:1) to give a colorless solid (12 mg, 59%).

HPLC (6 minute gradient) $t_R$=2.88 min; MS m/z 396 (M+H).

EXAMPLE 16

N-Cyclopropyl-4-methyl-3-(4-phenyl-quinazolin-7-yl)-benzamide

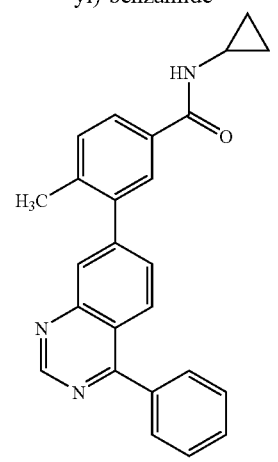

The mixture of 3'-Amino-4'-benzoyl-6-methyl-biphenyl-3-carboxylic acid cyclopropylamide from Example 15 (20 mg, 0.054 mmol) and formamide (2.9 mg, 0.065 mmol) in 0.7 mL acetic acid was stirred at 180° C. for 10 minutes in microwave. The solvents were removed under reduced pressure. The residue was dissolved in 50 mL of ethyl acetate and was washed with sat. aqueous NaHCO$_3$ (10 mL), water (10 mL), and brine (10 mL), dried over MgSO$_4$, and the solvents were evaporated. The residue was purified by preparative TLC sheet (methylene chloride:methanol=10:1) to give a colorless solid (4.6 mg, 22%)

HPLC (4 minute gradient) $t_R$=2.31 min; MS m/z 380 (M+H).

EXAMPLE 17

3'-Acetylamino-4'-benzoyl-6-methyl-biphenyl-3-carboxylic acid cyclopropylamide

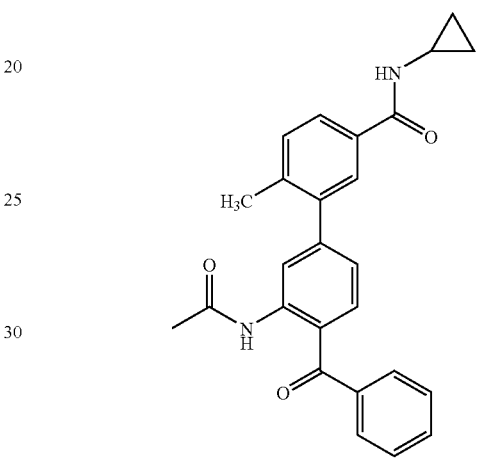

To a solution of the 3'-Amino-4'-benzoyl-6-methyl-biphenyl-3-carboxylic acid cyclopropylamide from Example 14 (21 mg, 0.057 mmol) and triethyl amine (29 mg, 0.284 mmol) in 1.5 mL methylene chloride was added acetic anhydride (8.7 mg, 0.085 mmol) at room temperature. The reaction mixture was stirred at that temperature for 6 hours. The mixture was diluted with 50 mL of ethyl acetate and was washed with sat. aqueous NaHCO$_3$ (10 mL), water (10 mL), and brine (10 mL), dried over MgSO$_4$, and the solvents were evaporated. The residue was purified by preparative TLC sheet (ethyl acetate:hexanes=1:1) to give a colorless solid (20 mg, 85%).

HPLC (4 minute gradient) $t_R$=2.27 min; MS m/z 413 (M+H).

The ability of the compounds provided herein to inhibit the synthesis or the activity of cytokines can be demonstrated using the following in vitro assays.

Biological Assays

Generation of p38 Kinases cDNAs of human p38α and β were cloned by PCR. The α and β cDNAs were subcloned into DEST2 plasmid (Gateway, InVitrogen). His$_6$-p38 fusion protein was expressed in *E. coli* and purified from bacterial lysates by affinity chromatography using Ni$^{+2}$-NTA-agarose. His$_6$-p38 protein was activated by incubating with constitutively active MKK6. Active p38 was separated from MKK6 by affinity chromatography. Constitutively active MKK6 was generated in a manner similar to Raingeaud et al. [*Mol. Cell. Biol.*, 1247-1255 (1996)].

TNF-α Production by LPS-Stimulated PBMCs

Heparinized human whole blood was obtained from healthy volunteers. Peripheral blood mononuclear cells (PBMCs) were purified from human whole blood by Accu-paque density gradient centrifugation and resuspended at a concentration of $5 \times 10^6$/ml in assay medium (RPMI medium containing 10% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% $CO_2$. Following incubation, the culture medium was collected and stored at −20° C.

THP-1 cells (TIB-202, ATCC) were washed and resuspended at a concentration of $1 \times 10^5$/ml in assay medium (RPMI medium containing 3% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% $CO_2$. Following incubation, the culture medium was collected and stored at −20° C.

TNF-α concentration in the medium was quantified using a standard ELISA kit (BioSource International, Camarillo, Calif.). Concentrations of TNF-α and $IC_{50}$ values for test compounds (concentration of compound that inhibited LPS-stimulated TNF-α production by 50%) were calculated by four parameter logistic curve (SigmaPlot, SPSS, Inc.).

p38α Assay

The p38α assay employed is based on measurement of ADP released in the reaction of interest through NADH oxidation obtained by coupling with pyruvate kinase and lactate dehydrogenase reactions. The assays were performed in 384-well UV-plates. The final volume was 25 uL prepared from the addition of 2.5 uL compound dissolved in 10% DMSO, 17.5 uL of assay buffer and 5 uL of ATP. Assay buffer contains the following reagents to give final concentration in the assay: 25 mM HEPES, 20 mM 2-glycerophosphate, pH 7.6, 10 mM $MgCl_2$, 0.1 mM sodium orthovanadate, 0.5 mM phosphoenolpyruvate, 0.12 mM NADH, 3.1 mg/ml LDH, 6.67 mg/ml pyruvate kinase, 0.25 mM peptide substrate, 2 mM DTT, 0.005% Tween 80 and 20 nM p38α kinase from Upstate. Test compounds are preincubated with p38α kinase for 60 min and the reaction started by addition of ATP to 0.15 mM final concentration. Reaction rates were measured at 340 nm using SpectraMax plate-reading spectrophotometer for 10 min at 37° C. Inhibition data were analyzed by non-linear least-squares regression using SigmaPlot.

The pharmacological results obtained in the above tests for products indicated in examples in the present application are given in the Table 1 below, the degrees of activities of the products being indicated by + signs according to the ranges of activity indicated in the table, i.e.:

TABLE 1

| Example No. | Activity (p-38)<br>+ $IC_{50}$ >10 µM<br>++ $IC_{50}$ 1–10 µM<br>+++ $IC_{50}$ <1 µM |
|---|---|
| 1 | +++ |
| 2 | +++ |
| 3 | +++ |
| 4 | +++ |

TABLE 1-continued

| Example No. | Activity (p-38)<br>+ $IC_{50}$ >10 µM<br>++ $IC_{50}$ 1–10 µM<br>+++ $IC_{50}$ <1 µM |
|---|---|
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |

TNF-α Production by LPS-Stimulated Mice

Mice (Balb/c female, 6-8 weeks of age, Taconic Labs; n=8/treatment group) were injected intraperitoneally with lipopolysaccharide (LPS) (50 ug/kg of E. coli strain 0111:B4, Sigma) suspended in sterile saline. Ninety minutes later, mice were sedated by $CO_2:O_2$ inhalation and a blood sample was obtained. Serum was separated and analyzed for TNF-α concentrations by commercial ELISA assay per the manufacturer's instructions (BioSource International). Test compounds were administered orally at various times before LPS injection. The compounds were dosed either as suspensions or as solutions in various vehicles or solubilizing agents.

We claim:

1. A compound having formula (I):

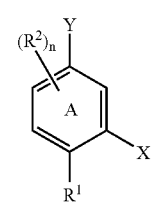

(I)

or a pharmaceutically acceptable salt thereof, wherein X is

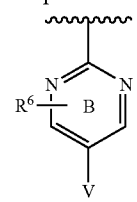

$R^1$ is halogen, lower alkyl;
$R^2$ is attached to any available carbon atom of the phenyl ring A and at each occurrence is alkyl;
n is 0 or 1;
Y is -L-$R^2$;
$R^3$ is hydrogen, alkyl, and cycloalkyl;
L is —C(═O)NH—, —NH(C═O)—;
V is -M-$R^{10}$;
M is —C(═O)$NR^4$—, —$NR^4$(C═O)—, —$NR^4$(C═O) $NR^4$—, —$NR^4SO_2$—, or —C(═O)—;
$R^4$ is each selected from hydrogen, lower alkyl and lower cycloalkyl;
$R^6$ at each occurrence is independently hydrogen, alkyl, —$NH_2$, or —$NMe_2$;

R¹⁰ is alkyl, alkoxyaralkyl, aryl, or —(CH₂)ₜ-D-(CH₂)ₑ—R¹³;

t is selected from 0, 1, 2 and 3; e is selected from 0, 1, 2 and 3;

D is selected from a bond, an optionally substituted heterocyclyl, an optionally substituted aryl, —O—, —S—, —(C=O)—, —NR⁴(C=O)—, —(C=O)NR⁴—, —S(O)—, SO₂NR⁴—, SO₂—, and —NR⁴—;

R¹³ is selected from an optionally substituted five- to seven-membered heterocyclic ring, an optionally substituted five- to seven-membered heteroaryl ring and an optionally substituted fused bicyclic ring; and wherein optionally substituted heterocyclyl, optionally substituted heteroaryl ring and optionally substituted fused bicyclic ring are heterocyclyl, heteroaryl ring and fused bicyclic ring which are unsubstituted or substituted by substituent selected from the group consisting of alkyl, arylalkyl, halo, hydroxy, oxo, alkanoyl, aryloxy, alkanoyloxy, amino, alkylamino, arylamino, aralkylamino, disubstituted amines in which the two amino substituents are selected from alkyl, aryl or aralkyl; akanoylamino, aroylamino, aralkanoylamino, substituted alkanoylamino, substituted arylamino, substituted aralkanoylamino, thiol, alkylthio, aralkylthio, alkylthiono, arylthiono, aralkylthiono, alkylsulfonyl, arylsulfonyl, aralkylsulfonyl, sulfonamido, substituted sulfonamido, nitro, cyano, carboxy, carbamyl, substituted carbamyl, alkoxybarbonyl, aryl, substituted aryl, guanidino, heterocyclyl, in which wherein the said substituent is further substituted, the further substituent is selected from alkyl, alkoxy, aryl and aralkyl; and wherein optionally substituted aryl is an aryl which is unsubstituted or substituted by one to four substituents selected from the group consisting of alkyl, halo, thrifluoromethoxy, trufluoromethyl, hydroxy, alkoxy, alkanoyl, alkanoyloxy, amino, arylamino, aralkylamino, dialkylamino, alkanocylamino, thiol, alkylthio, ureido, nitro, cyano, carboxy, carboxyalkyl, carbamyl, alkoxycarbonyl, alkylthiono, arylthiono, arylsulfonylamino, sulfonic acid, alkylsulfonyl, sulfonamido, and aryloxy; each of which may be further substituted with hydroxy, alkyl, alkoxy, aryl, or arylalkyl.

2. The compound of claim 1 having formula (III):

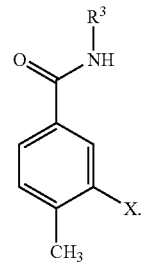

(III)

3. The compound of claim 1 having formula (V):

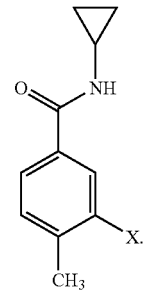

V

4. The compound of claim 1, wherein R⁶ is lower alkyl or hydrogen.

5. The compound of claim 1, wherein M is —C(=O)NR⁴—.

6. The compound of claim 1, wherein M is —C(=O)NH—.

7. The compound of claim 1, wherein R¹⁰ is 4-methoxybenzyl.

8. The compound of claim 1, wherein R¹ is lower alkyl.

9. The compound of claim 1, wherein R³ is lower alkyl or lower cycloalkyl.

10. The compound of claim 1, wherein R³ is Lower cycloalkyl.

11. The compound of claim 1, wherein R³ is cyclopropyl.

12. The compound of claim 1:
N-(4-Methoxybenzyl)-2-[(5-cyclopropylaminocarbonyl)-2-methylphenyl]-4-aminopyrimidine-5-carboxyamide.

13. A pharmaceutical composition, comprising a compound of claim 1 and a pharmaceutically acceptable carrier.

* * * * *